US012613249B2

(12) United States Patent

Multhaup et al.

(10) Patent No.: US 12,613,249 B2

(45) Date of Patent: Apr. 28, 2026

(54) USE OF Aβ34 TO ASSESS ALZHEIMER'S DISEASE PROGRESSION

(71) Applicant: THE ROYAL INSTITUTION FOR THE ADVANCEMENT OF LEARNING / MCGILL UNIVERSITY, Montréal (CA)

(72) Inventors: Gerhard Multhaup, Hampstead (CA); Adeola Shobo, Montreal (CA)

(73) Assignee: THE ROYAL INSTITUTION FOR THE ADVANCEMENT OF LEARNING / MCGILL UNIVERSITY, Montreal (CA)

( * ) Notice: Subject to any disclaimer, the term of this patent is extended or adjusted under 35 U.S.C. 154(b) by 963 days.

(21) Appl. No.: 17/323,312

(22) Filed: May 18, 2021

(65) Prior Publication Data

US 2021/0285971 A1 Sep. 16, 2021

Related U.S. Application Data

(63) Continuation of application No. PCT/CA2020/050432, filed on Apr. 2, 2020.

(60) Provisional application No. 62/829,284, filed on Apr. 4, 2019.

(51) Int. Cl.
 *C07K 16/18* (2006.01)
 *G01N 33/68* (2006.01)

(52) U.S. Cl.
 CPC ......... *G01N 33/6896* (2013.01); *C07K 16/18* (2013.01); *C07K 2317/34* (2013.01); *G01N 2333/4709* (2013.01); *G01N 2800/2821* (2013.01)

(58) Field of Classification Search
 CPC ..... G01N 33/68; G01N 33/6896; C07K 16/18
 See application file for complete search history.

(56) References Cited

U.S. PATENT DOCUMENTS

| | | | |
|---|---|---|---|
| 5,750,349 A | 5/1998 | Nobuhiro et al. | |
| 5,955,317 A | 9/1999 | Nobuhiro et al. | |
| 7,993,869 B2 | 8/2011 | Drijfhout et al. | |
| 10,024,871 B2 * | 7/2018 | Umek ................ | G01N 33/6896 |
| 2006/0205012 A1 * | 9/2006 | Debad ................ | G01N 33/6893 |
| | | | 435/7.1 |
| 2013/0273574 A1 * | 10/2013 | Kidd .................. | G01N 33/6896 |
| | | | 435/7.92 |

FOREIGN PATENT DOCUMENTS

| | | | | |
|---|---|---|---|---|
| WO | WO-2004058055 A2 * | 7/2004 | ......... | G01N 33/6803 |
| WO | 2019033050 | 2/2019 | | |

OTHER PUBLICATIONS

Pandya et al., Does Mild Cognitive Impairment Always Lead to Dementia? A Review, Journal of Neurological Sciences, 2016, 369, 57-62. (Year: 2016).*

Liebsch, F., Thesis, Identification of Novel Molecular Properties of the Alzheimer's Disease Beta-Secretase (BACE1) and Their Functional Consequences, Jul. 2017, McGill University, Montreal, Quebec, (i)-217; as well as, Appendix A-C: Papers in Press, 2017; 218-263. (Year: 2017).*

Braucker et al., Aβ42-oligomer Interacting Peptide (AIP) Neutralizes Toxic Amyloid-Aβ42 Species and Protects Synaptic Structure and Function, Scientific Reports, 2015, 5:15410, 1-15 (Year: 2015).*

McGill, Student Seminars, Integrated Program in Neuroscience, 2025, 1-60. Obtained online at: https://www.mcgill.ca/ipn/continuing/events/studentseminars on Mar. 20, 2025. (Year: 2025).*

Liebsch and Kulic, Aβ34 is a BACE1-derived degradation intermediate associated with amyloid clearance and Alzheimer's disease progression, Nature Communications, May 2019, 10(2240), 1-15. (Year: 2019).*

Aschenbrenner et al., Comparison of Plasma and CSF Biomarkers in Predicting Cognitive Decline, Annals of Clinical and Translational Neurology, 2022, 1739-1751. (Year: 2022).*

Cheng et al., Physiological β-Amyloid Clearance by the Liver and its Therapeutic Potential for Alzheimer's Disease, Acta Neuropahtologica, 2023, 145, 717-731. (Year: 2023).*

McGill University, Libraries, 2025, 1-2. Obtained online at: https://www.mcgill.ca/library/find/escholarship/submit on Jul. 2, 2025. (Year: 2025).*

McGill University, Graduate and Postdoctoral Studies, Doctoral Oral Defence Proceedings, 2025, 1-2. Obtained online at: https://www.mcgill.ca/gradsupervision/ timelines/exams/oral-defence#:~:text= Prepare%20to %20address-%20questions%20from, bit%20"outside% 20the %20box on Jun. 4, 2025. (Year: 2025).*

Caillava, C. et al. "Study on A[beta]34 biology and detection in transgenic mice brains". Neurobiology of Aging. vol. 35, No. 7, 2014. pp 1570-1581.

* cited by examiner

*Primary Examiner* — Amy M Bunker

(74) *Attorney, Agent, or Firm* — NORTON ROSE FULBRIGHT CANADA LLP

(57) ABSTRACT

It is provided an anti-Aβ34 antibody and its use for diagnosing Alzheimer's disease in a patient, comprising obtaining a sample from the patient, detecting the level of Aβ34 in the sample by contacting the sample with the anti-Aβ34 antibody and detecting binding between Aβ34 and the antibody, and diagnosing the patient with Alzheimer's disease when the presence of Aβ34 in the sample is detected, alone or in combination with detecting an amyloid deposition marker such as Aβ42 and determining the ratio of Aβ34/Aβ42.

8 Claims, 20 Drawing Sheets

Specification includes a Sequence Listing.

SEQUENCE LISTING

```
<160> NUMBER OF SEQ ID NOS: 7

<210> SEQ ID NO 1
<211> LENGTH: 366
<212> TYPE: DNA
<213> ORGANISM: Artificial Sequence
<220> FEATURE:
<223> OTHER INFORMATION: heavy chain variable region sequence of AB34
      antibody

<400> SEQUENCE: 1
gtgaagctgg tggagtctgg gggaggctta gtgaagcctg gagggtccct gaaactctcc        60
tgtgcagcct ctggattcac tttcagtacc tatgccatgt cttgggttcg ccagactcca       120
gagaagaggc tggagtgggt cgcatccatt agtagtggtg gtaacaccta ctatccagac       180
agtgtgaagg gccgattcac catctccaga gataatgcca ggcacatcct gtacctgcaa       240
atgagcagtc tgaggtctga ggacacggcc atgtattact gtgcaagaga ttcttattac       300
ttcggtaata gcgtttacta tgctatggac tactggggtc aaggaacctc agtcaccgtc       360
tcctca                                                                  366

<210> SEQ ID NO 2
<211> LENGTH: 122
<212> TYPE: PRT
<213> ORGANISM: Artificial Sequence
<220> FEATURE:
<223> OTHER INFORMATION: heavy chain variable region sequence of AB34
      antibody

<400> SEQUENCE: 2
```

-continued

```
Val Lys Leu Val Glu Ser Gly Gly Gly Leu Val Lys Pro Gly Gly Ser
1               5                   10                  15

Leu Lys Leu Ser Cys Ala Ala Ser Gly Phe Thr Phe Ser Thr Tyr Ala
            20                  25                  30

Met Ser Trp Val Arg Gln Thr Pro Glu Lys Arg Leu Glu Trp Val Ala
        35                  40                  45

Ser Ile Ser Ser Gly Gly Asn Thr Tyr Tyr Pro Asp Ser Val Lys Gly
    50                  55                  60

Arg Phe Thr Ile Ser Arg Asp Asn Ala Arg His Ile Leu Tyr Leu Gln
65                  70                  75                  80

Met Ser Ser Leu Arg Ser Glu Asp Thr Ala Met Tyr Tyr Cys Ala Arg
            85                  90                  95

Asp Ser Tyr Tyr Phe Gly Asn Ser Val Tyr Tyr Ala Met Asp Tyr Trp
            100                 105                 110

Gly Gln Gly Thr Ser Val Thr Val Ser Ser
            115                 120
```

<210> SEQ ID NO 3
<211> LENGTH: 339
<212> TYPE: DNA
<213> ORGANISM: Artificial Sequence
<220> FEATURE:
<223> OTHER INFORMATION: light chain variable region sequence of AB34
      antibody

<400> SEQUENCE: 3

```
gatgttgtga tgacccagac tccattcatt ttgtcggtga ccatcggaca accagcctcc      60
atctcttgca agtcaagtca gagcctctta gatagtgatg gaaaaacata tttgaattgg     120
ttgtttcaga ggccaggcca gtccccaaag cggctaatct atcaggtgtc taaagtggac     180
gctggagtcc ctgacaggtt ctctggcagt ggatcaggga cagatttcac actgaaaatc     240
agcagagtgg aggctgagga tttgggaatt tattattgct ggcaaggtac acattttcct     300
cggacgttcg gtggaggcac caaactggaa atcaaacgg                            339
```

<210> SEQ ID NO 4
<211> LENGTH: 113
<212> TYPE: PRT
<213> ORGANISM: Aritificial sequence
<220> FEATURE:
<223> OTHER INFORMATION: light chain variable region sequence of AB34
      antibody

<400> SEQUENCE: 4

```
Asp Val Val Met Thr Gln Thr Pro Phe Ile Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Phe Gln Arg Pro Gly Gln Ser
        35                  40                  45

Pro Lys Arg Leu Ile Tyr Gln Val Ser Lys Val Asp Ala Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Trp Gln Gly
            85                  90                  95

Thr His Phe Pro Arg Thr Phe Gly Gly Gly Thr Lys Leu Glu Ile Lys
            100                 105                 110
```

-continued

```
Arg

<210> SEQ ID NO 5
<211> LENGTH: 34
<212> TYPE: PRT
<213> ORGANISM: human
<220> FEATURE:
<223> OTHER INFORMATION: Human AB34 sequence

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu

<210> SEQ ID NO 6
<211> LENGTH: 8
<212> TYPE: PRT
<213> ORGANISM: Artificial sequence
<220> FEATURE:
<223> OTHER INFORMATION: Synthetic AIP

<400> SEQUENCE: 6

Arg Gly Thr Phe Glu Gly Lys Phe
1               5

<210> SEQ ID NO 7
<211> LENGTH: 8
<212> TYPE: PRT
<213> ORGANISM: Aritificial sequence
<220> FEATURE:
<223> OTHER INFORMATION: Scrambled AIP

<400> SEQUENCE: 7

Glu Phe Arg Lys Phe Thr Gly Gly
1               5
```

USE OF Aβ34 TO ASSESS ALZHEIMER'S DISEASE PROGRESSION

CROSS-REFERENCE TO RELATED APPLICATIONS

This application is a continuation of International Patent Application Number PCT/US2020/050432 filed on Apr. 2, 2020, which claimed priority to U.S. Provisional Patent Application No. 62/829,284 filed Apr. 4, 2019, the contents of both of which said applications are incorporated herein by reference in their entirety.

TECHNICAL FIELD

It is provided an anti-Aβ34 antibody and its use for detecting Alzheimer's disease.

BACKGROUND

The pathogenesis of Alzheimer's disease (AD) involves a heterogeneous mixture of amyloid-β (Aβ) peptides and amyloid plaque formation in the brain. Sequential cleavage of the amyloid precursor protein (APP) by β-secretase (BACE1) and the γ-secretase complex results in the generation of Aβ species of varying lengths, e.g. Aβ38, Aβ40, and Aβ42. More neurotoxic than Aβ38 or Aβ40, the Aβ42 peptide is prone to form aggregated amyloid oligomers (i.e. precursor to larger fibrils), which are thought to contribute to plaque formation and cognitive decline.

To block the first step of amyloid production, the pharmaceutical industry has focused on inhibitors of BACE1 as a therapeutic strategy for AD. However, BACE1 inhibitors have failed in clinical trials due to side effects, possible toxicity, or the absence of beneficial cognitive outcomes. The lack of success may also relate to the timing of administration, since treatments in the symptomatic stage might be too late. Recent evidence suggests that pre-symptomatic administration may be beneficial, given that BACE1 inhibitor treatment had a strong impact on the formation of new plaques in a transgenic AD mouse model, whereas the growth of already existing plaques was only mildly slowed. WO2009143935 discloses a general method of screening for a therapeutic agent useful in the prophylaxis treatment of AD.

BACE1 levels are elevated in the neocortex of AD patients. Perhaps as a pathological response to fibrillar Aβ, the accumulation of BACE1 in the vicinity of amyloid plaques can enhance local Aβ generation. However, excess BACE1 activity can also lead to (i) alternative APP processing at the β'-site, generating metabolically labile Aβ11-X peptides, or (ii) Aβ degradation, by catalyzing the C-terminal truncation of Aβ40 and Aβ42 into the non-amyloidogenic, metabolically labile Aβ34. These additional and alternative BACE1-mediated cleavages could explain the unexpected finding that the total amount of deposited Aβ is lowered in the brain of transgenic mice overexpressing human BACE1. In human and canine in vivo studies, cerebrospinal fluid (CSF) levels of Aβ34 decline with pharmacological BACE1 inhibition, most likely due to an interruption of the BACE1-mediated degradation of Aβ40 and Aβ42. However, the amyloidolytic roles of BACE1 in Aβ metabolism are currently not well defined, either in health (i.e. physiological homeostasis) or disease (i.e. AD pathogenesis).

While most forms of autosomal dominant familial AD are associated with increased production and cerebral deposition of Aβ42, the pathological cascade of sporadic AD appears instead to be triggered by impaired Aβ degradation and clearance. Aβ clearance from the brain can occur by any of several mechanisms including interstitial fluid drainage, cellular uptake, and passive elimination. Enzymatic degradation can also generate specific patterns of soluble Aβ peptides in the CSF, as mediated by Aβ degrading enzymes (ADEs), which include metalloprotease family members such as endothelin-converting enzyme (ECE), insulin-degrading enzyme (IDE), and neprilysin (NEP). Results obtained with 18O-labeling mass spectrometry demonstrated that the Aβ peptide pattern in CSF is not generated by proteolytic activities in CSF itself—except in the acute phase of a bacterial meningitis—but Aβ fragments are likely generated prior to entering the CSF.

The normal clearance rate for Aβ40 or Aβ42 in human CSF is estimated to be ~8% per hour, but clearance is impaired by approximately 30% in AD patients. Aβ stable isotope labeling kinetics (SILK) studies found that production and clearance of soluble Aβ isoforms are similar for Aβ38 and Aβ40, but Aβ42 turnover is altered with increasing age and amyloidosis.

Currently, a diagnosis of possible or probable AD is typically made based on clinical symptoms. In order to improve the treatment of AD, there is a need to be provided with means to accurately diagnose the disease early in its course and to accurately monitor the progression of the disease.

There is thus still a need to be provided with new means to assess AD samples.

SUMMARY

One aim of the present disclosure is to provide an anti-Aβ34 antibody for detecting prodromal stages of dementia.

In an embodiment, the antibody described herein is for detecting progression of Alzheimer's disease.

In another embodiment, the antibody specifically binds to an epitope of Aβ34 protein consisting of SEQ ID NO: 5.

In a further embodiment, the antibody specifically binds to the C-terminal end of Aβ34.

In an embodiment, the antibody is a humanized antibody, a monoclonal antibody or a polyclonal antibody.

In another embodiment, the antibody is a mouse antibody, a goat antibody, a human antibody or a rabbit antibody.

In an embodiment, the antibody comprises an epitope binding fragment selected from the group consisting of: Fv, F(ab') and F(ab')$_2$.

In another embodiment, the antibody comprises a heavy chain variable region encoded by the nucleotide sequence set forth in SEQ ID NO: 1.

In a further embodiment, the antibody comprises a heavy chain variable region consisting of SEQ ID NO: 2.

In an additional embodiment, the antibody comprises a light chain variable region encoded by the nucleotide sequence set forth in SEQ ID NO: 3.

In another embodiment, the antibody comprises a light chain variable region consisting of SEQ ID NO: 4.

It is provided an antibody or a functional fragment thereof, comprising at least one of a) heavy chain encoded by the DNA sequence consisting of SEQ ID NO: 1; b) a heavy chain amino acid sequence consisting of SEQ ID NO: 2; c) a light chain encoded by the DNA sequence consisting of SEQ ID NO: 3; d) a light chain amino acid sequence consisting of SEQ ID NO: 4; e) a sequence with at least 70% sequence, preferably at least 80% sequence identity, more preferably at least 85% sequence identity, most preferably at least 90% sequence identity to a), b) c) or d); and f) a combination thereof.

In an embodiment, the antibody encompassed herein is a neo-epitope antibody.

It is also provided a composition comprising the antibody as described herein and a carrier.

In an embodiment, the carrier is a saline solution, a buffered saline solution, dextrose, water, glycerol, ethanol, or combinations thereof.

It is provided an hybridoma cell line producing the antibody as defined herein.

It is further provided a method of diagnosing early Alzheimer's disease in a patient, the method comprising obtaining a sample from the patient, and detecting the level of Aβ34 in the sample by contacting the sample with an anti-Aβ34 antibody and detecting binding between Aβ34 and the antibody, wherein the level of Aβ34 in the sample is indicative that the patient has Alzheimer's disease or will develop AD.

In an embodiment, the sample is a liquid sample or a solid sample.

In a further embodiment, the sample is a cerebrospinal fluid sample or serum.

In an embodiment, the method described herein further comprises a step of detecting the level of an amyloid deposition marker in the sample.

In an embodiment, the amyloid deposition marker is tau, Aβ42 or a combination thereof.

In another embodiment, the method described herein further comprises the steps of detecting the level of Aβ42 in the sample by contacting the sample with an anti-Aβ42 antibody and detecting binding between Aβ42 and the antibody, and measuring the ratio of Aβ34/Aβ42, wherein the diagnosing of the patient is made by the measuring of the Aβ34/Aβ42 ratio in the sample.

In an embodiment, the measuring of the Aβ34/Aβ42 ratio in the sample detects mild cognitive impairment (MCI) in said patient.

In another embodiment, the measuring of the Aβ34/Aβ42 ratio in the sample detects MCI patient that will develop dementia.

In a further embodiment, the patient is at stage 0, 1 or 2 of Alzheimer.

In an embodiment, it is encompass detecting a level of Aβ34/Aβ42 ratio >0.245.

In another embodiment, the level of Aβ34 are measured by immunoassay.

In an embodiment, the anti-Aβ34 antibody further comprises a fluorochrome or a labeling.

In an embodiment, the immunoassay is a radioimmunoassay, a Western blot assay, an immunofluorescence assay, an enzyme immunoassay, an immunoprecipitation assay, a chemiluminescence assay, an electrochemiluminescence assay, an immunohistochemical assay, an immunoelectrophoresis assay, a dot blot assay, or a slot blot assay.

It is also provided a reagent kit comprising an anti-Aβ34 antibody for the diagnosis of Alzheimer disease or prodromal stages in the method described herein.

It is further provided an anti-Aβ34 antibody comprising a heavy chain variable region encoded by the nucleotide sequence set forth in SEQ ID NO: 1 and a light chain variable region encoded by the nucleotide sequence set forth in SEQ ID NO: 3.

In another embodiment, the heavy chain variable region consists of SEQ ID NO: 2 and the light chain variable region consists of SEQ ID NO: 4.

In a further embodiment, it is provided that the patient diagnosed with early Alzheimer's disease is treated by administering a synthetic 8-amino acid Abeta42-oligomer Interacting Peptide (AIP).

In an embodiment, the AIP peptide comprises SEQ ID NO: 6 or SEQ ID NO: 7.

In a further embodiment, the synthetic AIP peptide is a peptide consisting of L-amino acids of SEQ ID NO: 6 or D-amino acids of SEQ ID NO: 7.

In another embodiment, the synthetic AIP peptide is D-AIP consisting of D-amino acids of SEQ ID NO: 6.

In an embodiment, the D-AIP is administered orally.

BRIEF DESCRIPTION OF THE DRAWINGS

Reference will now be made to the accompanying drawings.

9 phate buffered saline (PBS) as control were spiked into mouse liver S9-fraction and incubated for 24 h at 37° C. (lower panel) and the non-incubated spiked served as control (upper panel). MALDI-TOF MS spectra showed that D-AIP (941 m/z) was relatively stable over 24 h in the mouse liver S9-fraction whereas L-AIP was degraded under the same condition as its signal (941 m/z) could no longer be detected.

Figure 18:
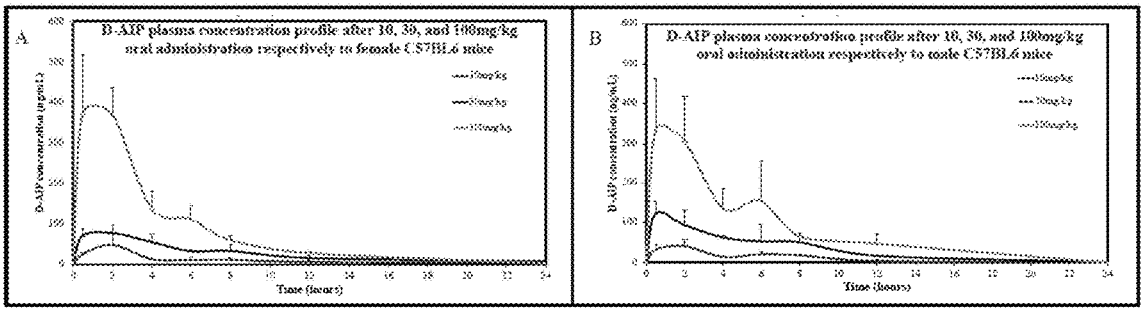

FIG. 18 illustrates the D-AIP concentration profiles in plasma, wherein D-AIP plasma concentration-time profiles after a single oral DAIP dose of 10 mg/kg (red), 30 mg/kg (black) and 100 mg/kg (green) respectively to 7-9 weeks old female (A) and male (B) C57BL/6 mice, wherein D-AIP concentrations in plasma were measured by LC-MS quantification of plasma samples taken from dosed animals between 0.5 h to 24 h at seven respective time points, and the highest concentration measured in the plasma was 372.25 ng/mL in female and 332.51 ng/ml in male mice that was reached at 0.5 h after single oral dose of 100 mg/kg with an average of 3 animals (n=3) in each group.

Figure 19:
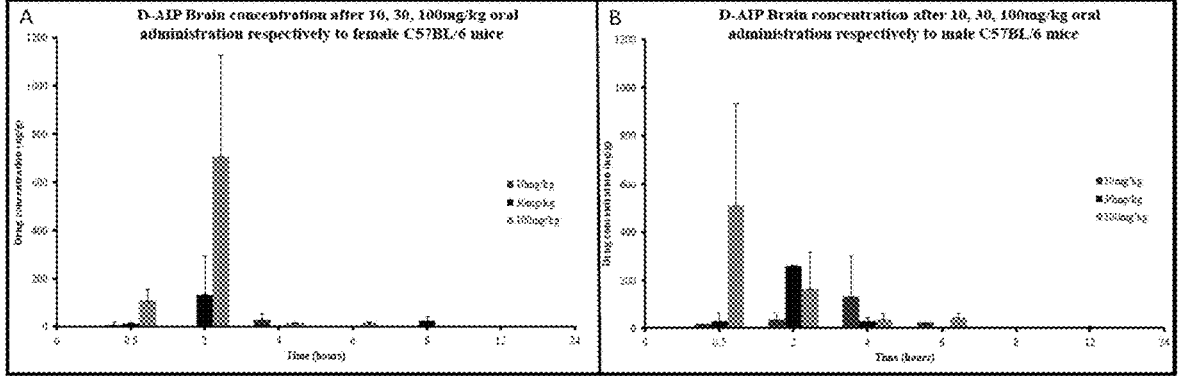

FIG. 19 illustrates D-AIP concentration profiles in brain, wherein time dependent alterations of D-AIP concentrations in brain homogenates after a single oral D-AIP dose of 10 mg/kg (red), 30 mg/kg (black) and 100 mg/kg (green) from 7-9 weeks old female (A) and male (B) C57BL/6 mice, the quantification was done by LC-MS measurements, and D-AIP crossed the BBB and reached the brain of both female and male mice treated with various single oral doses as indicated in the figure, data averaged from 3 animals (n=3).

Figure 20:
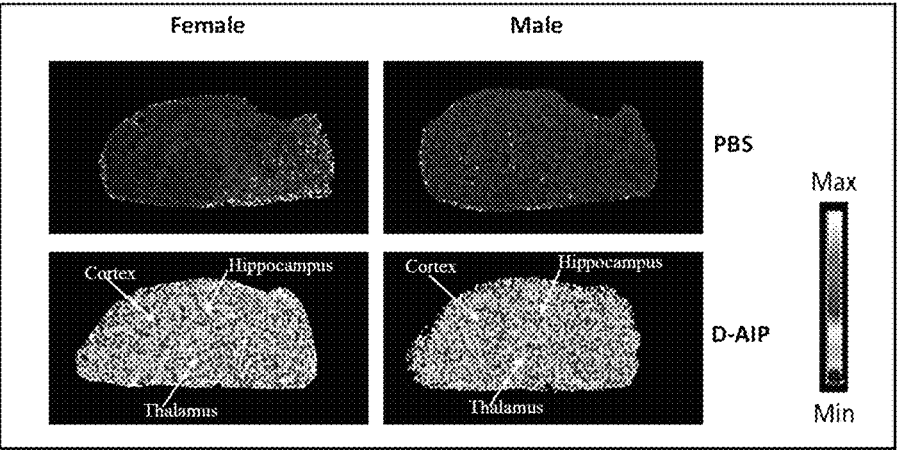

FIG. 20 illustrates the brain distribution of D-AIP wherein MALDI-TOF-MSI analysis of label-free D-AIP in sagittal brain sections of 7-9 weeks old female and male C57BL/6 mice single orally dosed with PBS or D-AIP (10 mg/kg) and sacrificed 4 h post-administration, showing representative images acquired using MALDI-TOF imaging technique which confirms the successful entrance of D-AIP (single oral D-AIP dose of 10 mg/kg and PBS treated control) into different brain regions of treated mice, and that D-AIP is distributed across cortex, hippocampus, thalamus and different other brain regions.

Figure 21:
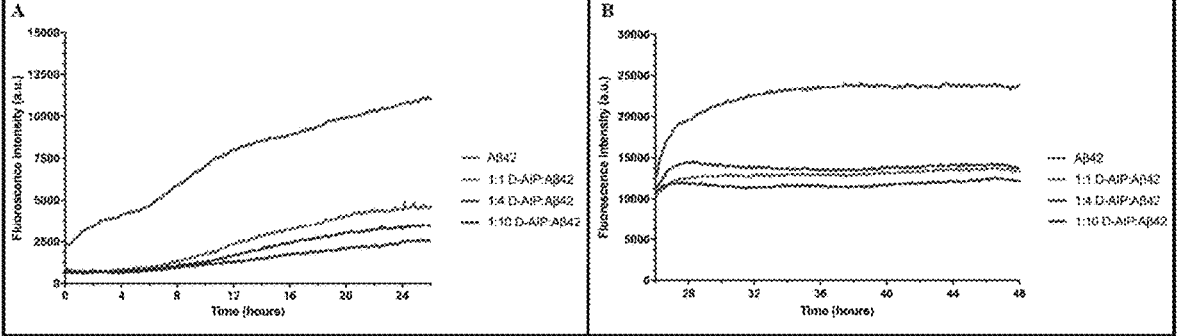

FIG. 21 illustrates the treatment of freshly dissolved or 24 h preformed aggregates treated with D-AIP, wherein freshly monomerized Aβ42 peptide (A) and aggregates of Aβ42 (B) incubated at room temperature with or without D-AIP at a molar ratio of 1:1, 1:4 and 1:10 (D-AIP:Aβ42) respectively, data are shown as means of three independent experiments (n=3).

Figure 22:
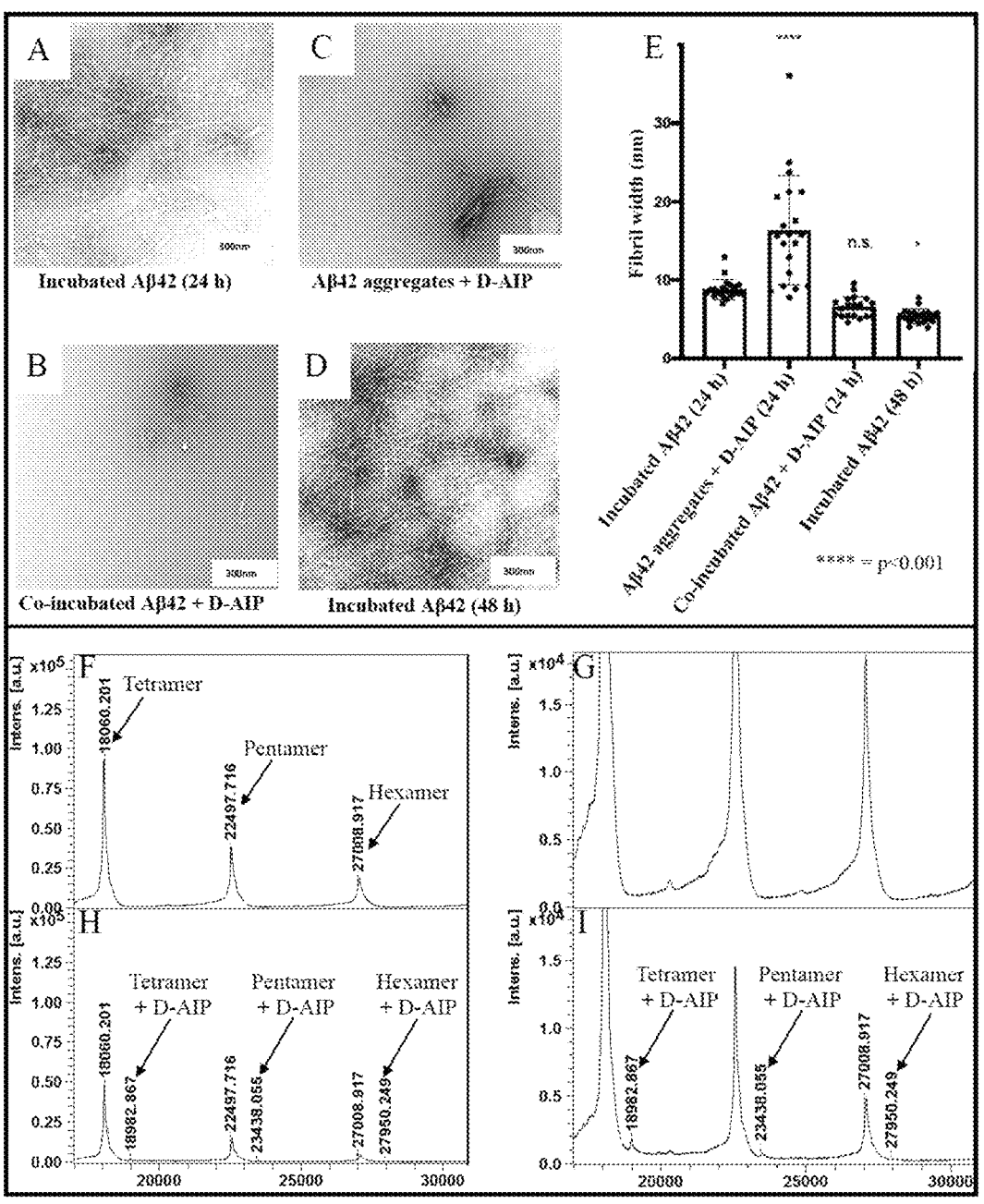

FIG. 22 illustrates interactions of D-AIP with Aβ42 aggregates, wherein TEM images of Aβ42 with or without D-AIP and the quantification of the fibril widths are shown in (A) freshly monomerized Aβ42 incubated for 24 h, (B) Aβ42 aggregates coincubated with D-AIP for 24 h, (C) freshly monomerized Aβ42 co-incubated with D-AIP, (D) freshly monomerized Aβ42 incubated for 48 h, (E) representative chart for the quantification of fibril widths, the lower panels are the MALDI-TOF MS spectrums of residue of (F) incubated Aβ42 peptide and its enlarged view (G), which revealed low order oligomers like the tetramers (18060 m/z), pentamers (22497 m/z) and hexamers (27008 m/z) of the Aβ42 peptide, respective MALDI-TOF MS spectrum (H) represents the residue obtained after Aβ42 aggregates were co-incubated with D-AIP for 24 h and its enlarged view (I).

DETAILED DESCRIPTION

It is provided an anti-Aβ34 antibody for detecting prodromal stages of dementia.

Imbalance between the production and clearance of amyloid-β (Aβ) peptides is likely a major factor in the pathogenesis of Alzheimer's disease (AD). The beta-site APP cleaving enzyme 1 (BACE1 or β-secretase) is known primarily for its initial cleavage of the amyloid precursor protein (APP), which ultimately leads to the generation of Aβ peptides. It is provided herein evidence that altered BACE1 expression levels and enzyme activity impact the degradation of Aβ40 and Aβ42 into a common Aβ34 intermediate.

It is known that Aβ34 is a common intermediate in the enzymatic processing of two distinct Aβ degradation pathways. The levels and metabolism of Aβ34 in the brains of BACE1−/−, BACE1+/−, and BACE1+/+ (wild type) mice, in brain and CSF of wild type rats treated with a BACE1 specific inhibitor, a cultured human neuronal cell line (SH-SY5Y), and CSF samples from individuals at various clinical stages of AD were assessed and provided herein. A custom, ultra-sensitive Meso Scale Discovery (MSD) electrochemiluminescence assay was developed, using a novel monoclonal neo-epitope antibody that binds specifically to the C-terminus of Aβ34 with nanomolar affinity. It is demonstrated herein that cerebral BACE1 levels are limiting for Aβ34 generation in vivo. Specifically, in well-characterized clinical groups, CSF levels of Aβ34 were notably elevated in individuals with mild cognitive impairment (MCI) who later progressed to AD dementia. Compared to the classical Aβ40/Aβ42 ratio (i.e. the current 'gold standard' of amyloid deposition in clinical practice), the Aβ34/Aβ42 ratio described here improved the ability to distinguish between individuals with MCI who later converted to AD from those who did not. Among cognitively normal individuals at risk for AD, an elevated CSF-Aβ34/Aβ42 ratio was detected together with current biomarkers of pre-clinical AD, such as elevated CSF levels of total-tau and phosphorylated ($P_{181}$)-tau. It is also described that the overall Aβ clearance rates positively correlated with CSF-Aβ34 levels in amyloid positive individuals.

It is thus provided a novel monoclonal neo-epitope antibody that binds specifically to the C-terminus of Aβ34 with nanomolar affinity. The antibody encompassed herein comprises the following heavy chain variable region sequence: Nucleotide Sequence:

(SEQ ID NO: 1)

GTGAAGCTGGTGGAGTCTGGGGGAGGCTTAGTGAAGCCTGGAGGGTCCC

TGAAACTCTCCTGTGCAGCCTCTGGATTCACTTTCAGTACCTATGCCAT

GTCTTGGGTTCGCCAGACTCCAGAGAAGAGGCTGGAGTGGGTCGCATCC

ATTAGTAGTGGTGGTAACACCTACTATCCAGACAGTGTGAAGGGCCGAT

TCACCATCTCCAGAGATAATGCCAGGCACATCCTGTACCTGCAAATGAG

CAGTCTGAGGTCTGAGGACACGGCCATGTATTACTGTGCAAGAGATTCT

TATTACTTCGGTAATAGCGTTTACTATGCTATGGACTACTGGGGTCAAG

GAACCTCAGTCACCGTCTCCTCA.

Translated Protein Sequence:

```
                                          (SEQ ID NO: 2)
VKLVESGGGLVKPGGSLKLSCAASGFTFSTYAMSWVRQTPEKRLEWVAS

ISSGGNTYYPDSVKGRFTISRDNARHILYLQMSSLRSEDTAMYYCARDS

YYFGNSVYYAMDYWGQGTSVTVSS.
```

The antibody encompassed herein comprises the following light chain variable region sequence:
Nucleotide Sequence:

```
                                          (SEQ ID NO: 3)
GATGTTGTGATGACCCAGACTCCATTCATTTTGTCGGTGACCATCGGAC

AACCAGCCTCCATCTCTTGCAAGTCAAGTCAGAGCCTCTTAGATAGTGA

TGGAAAAACATATTTGAATTGGTTGTTTCAGAGGCCAGGCCAGTCCCCA

AAGCGGCTAATCTATCAGGTGTCTAAAGTGGACGCTGGAGTCCCTGACA

GGTTCTCTGGCAGTGGATCAGGGACAGATTTCACACTGAAAATCAGCAG

AGTGGAGGCTGAGGATTTGGGAATTTATTATTGCTGGCAAGGTACACAT

TTTCCTCGGACGTTCGGTGGAGGCACCAAACTGGAAATCAAACGG.
```

Translated Protein Sequence:

```
                                          (SEQ ID NO: 4)
DVVMTQTPFILSVTIGQPASISCKSSQSLLDSDGKTYLNWLFQRPGQSP

KRLIYQVSKVDAGVPDRFSGSGSGTDFTLKISRVEAEDLGIYYCWQGTH

FPRTFGGGTKLEIKR.
```

It is thus encompassed an antibody or a functional fragment thereof, comprising at least one of:
    a) heavy chain encoded by the DNA sequence consisting of SEQ ID NO: 1;
    b) a heavy chain amino acid sequence consisting of SEQ ID NO: 2;
    c) a light chain encoded by the DNA sequence consisting of SEQ ID NO: 3;
    d) a light chain amino acid sequence consisting of SEQ ID NO: 4;
    e) a sequence with at least 70% sequence identity, preferably 80%, more preferably 85%, more preferably 90% sequence identity to a), b) c) or d); and
    f) a combination thereof.
In a further aspect, the present disclosure provides a composition comprising the antibody described herein in admixture with a physiologically or pharmaceutically acceptable excipient.

More particularly, the antibody specifically binds to an epitope on Aβ34, more preferably to the C-terminus of Aβ34.

In a particular embodiment, the antibody recognizes the epitope defined as:

```
                                          (SEQ ID NO: 5)
     DAEFRHDSGYEVHHQKLVFFAEDVGSNKGAIIGL.
```

The anti-Aβ34 described herein may be employed in admixture with a suitable physiological or pharmaceutical carrier. Such compositions comprise a therapeutically effective amount of the antibody, and a physiologically or a pharmaceutically acceptable carrier or excipient. Such a carrier includes but is not limited to saline, buffered saline, dextrose, water, glycerol, ethanol, and combinations thereof. The formulation should suit the mode of administration.

In an embodiment, the anti-Aβ34 encompassed herein is a monoclonal antibody, a polyclonal antibody, or a humanized antibody.

In a further embodiment, the antibody is a mouse antibody, a goat antibody, a human antibody or a rabbit antibody.

In a particular embodiment, the antibody comprises an epitope binding fragment that is selected from: Fv and/or F(ab') and/or F(ab')2. In particular, the antibody comprises an epitope-binding single chain antibody.

It is also encompassed herein are hybridoma cell lines producing the antibodies disclosed herein. Methods of producing hybridoma cells lines are well known. The immunizing agent typically includes the desired polypeptide or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are then transformed mammalian cells, particularly myeloma cells of rodent, bovine and human origin. Usually, rat or mouse myeloma cell lines are employed. The hybridoma cells are cultured in a suitable culture medium that can contains one or more substances that inhibit the growth or survival of the unfused, immortalized cells. Preferred immortalized cell lines are those that fuse efficiently, support stable high level expression of antibody by the selected antibody-producing cells, and are sensitive to a medium. The culture medium in which the hybridoma cells are cultured is then be assayed for the presence of monoclonal antibodies. The binding specificity of monoclonal antibodies produced by the hybridoma cells is normally determined by immuno-precipitation or by an in vitro binding assay, such as radio-immunoassay (RIA) or enzyme-linked immunoabsorbent assay (ELISA). Such techniques and assays are known in the art.

After the desired hybridoma cells are identified, the clones are subcloned by limiting dilution procedures and grown by standard methods. Suitable culture media for this purpose includes, for example, Dulbecco's Modified Eagle's Medium and RPMI-1640 medium. Alternatively, the hybridoma cells are grown in vivo as ascites in a mammal. The monoclonal antibodies secreted by the subclones are isolated or purified from the culture medium or ascites fluid by conventional immunoglobulin purification procedures.

As encompassed herein, the anti-Aβ34 antibodies are monovalent neo-epitopes antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking. In vitro methods are also suitable for preparing monovalent antibodies. Digestion of antibodies to produce fragments thereof, particularly, Fab fragments, can be accomplished using routine techniques known in the art.

Using human cerebrospinal fluid (CSF) samples from the Amsterdam Dementia Cohort, it is demonstrated that Aβ34 is elevated in individuals with mild cognitive impairment (MCI) who later progressed to dementia (irrespective of age, APOE ε4 carrier status, or sex). Furthermore, Aβ34 levels correlate with the overall Aβ clearance rates in amyloid positive individuals. Using human CSF samples from the PREVENT-AD cohort (cognitively normal individuals at risk for AD), it is further demonstrated that the novel Aβ34/Aβ42 ratio, representing Aβ degradation and cortical deposition, associates with well-established pre-clinical markers of neurodegeneration.

Accordingly, it is provided that treating patients with BACE1 inhibitors may impede amyloid clearance in the brain by blocking the conversion of Aβ40 and Aβ42 to the degradation intermediate Aβ34. It is thus proposed that Aβ34 represents an important new marker of amyloid clearance and anticipate that the ultra-sensitive multiplex assay described herein can be used for the characterization of Aβ turnover in clinical samples.

Figure 1:
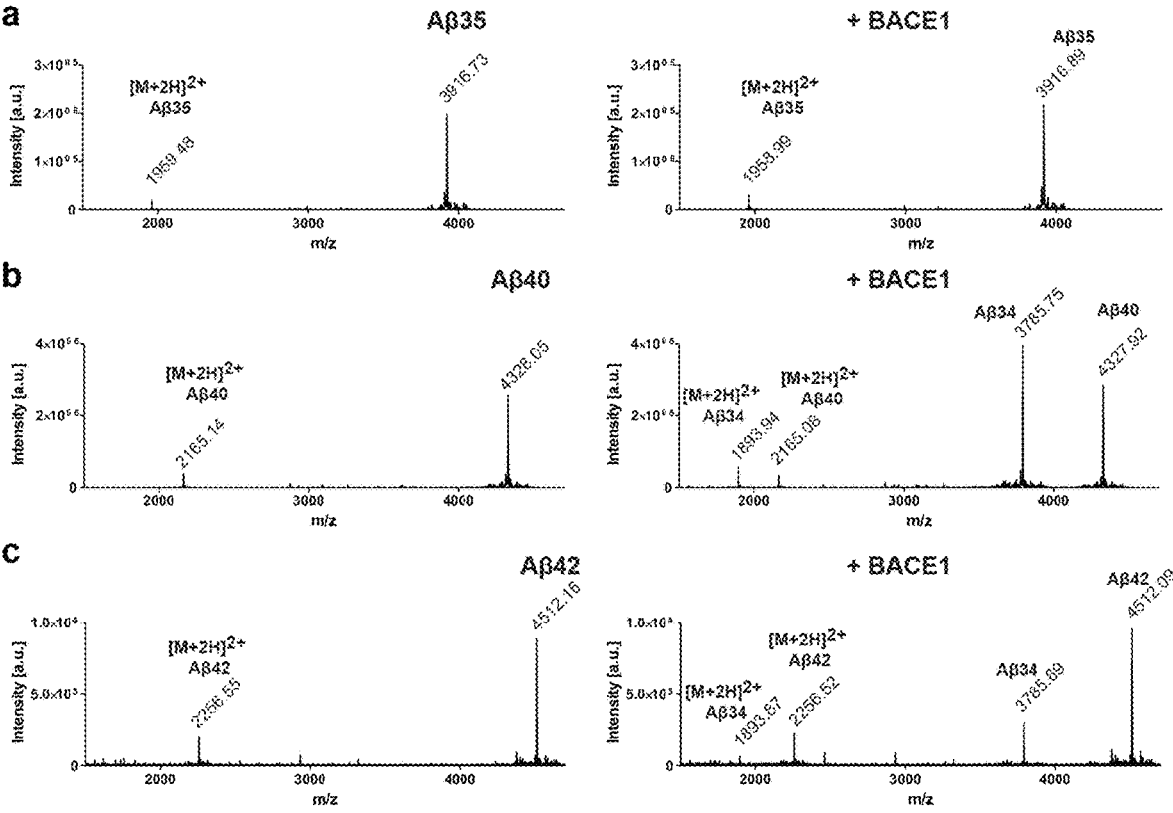
FIG. 1 illustrates BACE1-mediated Aβ degradation in vitro, showing cleavage of Aβ40 and Aβ42 by BACE1 in vitro analyzed by MALDI-MS, wherein data were collected from 3 independent experiments, representative MALDI-MS spectra for Aβ35 (a), Aβ40 (b), and Aβ42 (c), in the absence (left) or presence (right) of BACE1.
Figure 2:
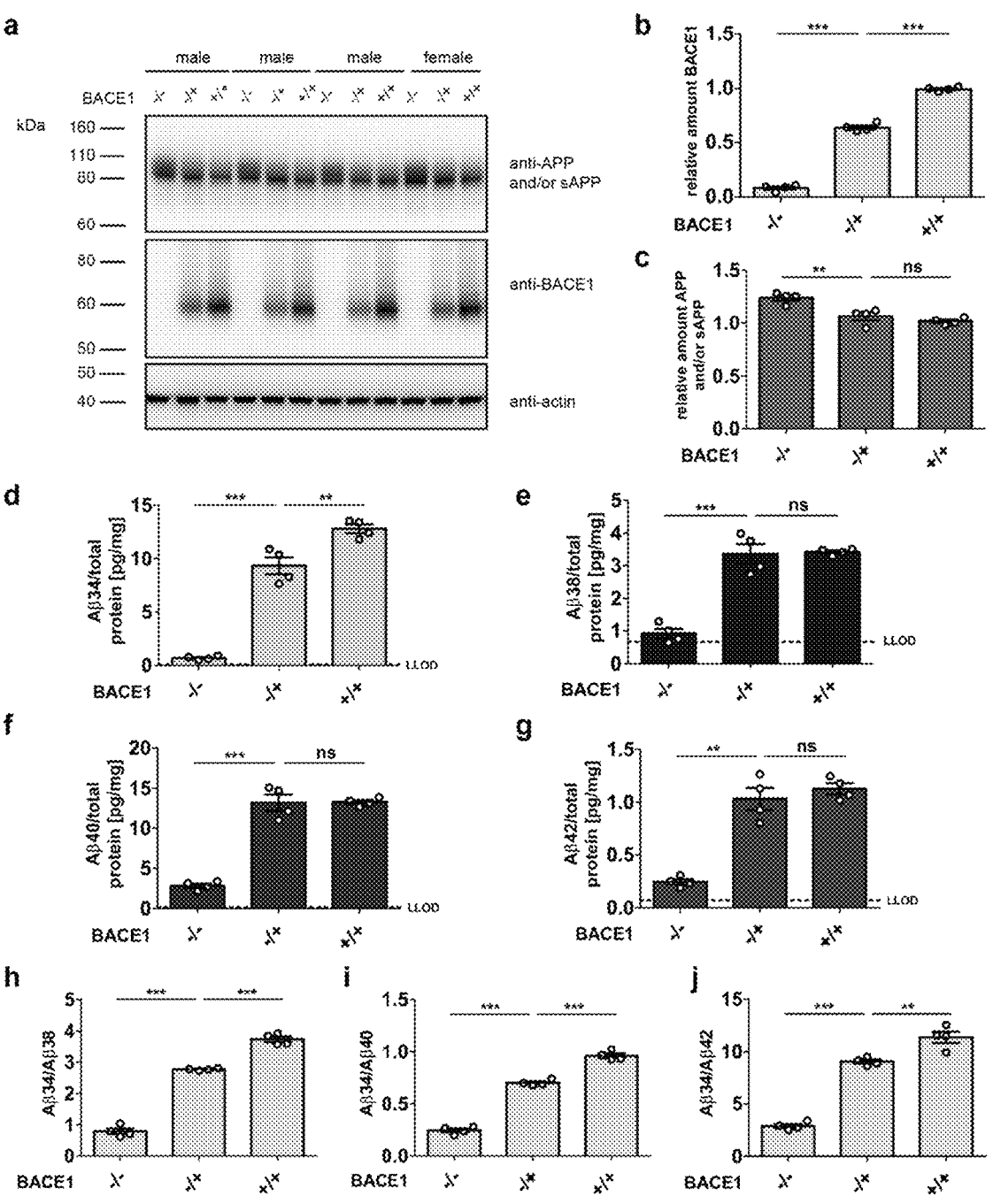
FIG. 2 illustrates endogenous BACE1 generates Aβ34 in the murine brain, showing endogenous levels of murine APP and/or sAPP, BACE1, and Aβ in BACE1−/−, BACE1+/−, and wild type littermates (+/+). Western blot of endogenous APP and/or sAPP and BACE1 expression in male and female mice are shown in (a) and corresponding quantification of relative protein amounts of BACE1 in (b) and APP and/or sAPP in (c). Quantification (pg/mg total protein) are shown of absolute amounts of Aβ34 in (d), Aβ38 in (e), Aβ40 in (f), and Aβ42 in (g) as determined by custom 4-plex MSD multiplexing assays. Ratios of Aβ34/Aβ38 in (h), Aβ34/Aβ40 in (i), and Aβ34/Aβ42 in (j) are displayed. Statistics: (b) 1-WAY ANOVA, $F_{(2,9)}=1021$, $p<0.0001$, (c) 1-WAY ANOVA, $F_{(2,9)}=17.28$, $p<0.001$, (d) 1-WAY ANOVA, $F_{(2,9)}=145.7$, $p<0.0001$, (e) 1-WAY ANOVA, $F_{(2,9)}=53.68$, $p<0.0001$, (f) 1-WAY ANOVA, $F_{(2,9)}=95.65$, $p<0.0001$, (g) 1-WAY ANOVA, $F_{(2,9)}=49.79$, $p<0.0001$, (h) 1-WAY ANOVA, $F_{(2,9)}=425.2$, $p<0.0001$, (i) 1-WAY ANOVA, $F_{(2,9)}=378.0$, $p<0.0001$, (j) 1-WAY ANOVA, $F_{(2,9)}=167.6$, $p<0.0001$. Bars and error bars indicate mean±s.e.m. Tukey's post-hoc tests were performed for pairwise comparisons; selected comparisons are highlighted *$p<0.001$, $p<0.01$, *$p<0.05$, ns=non-significant $p>0.05$. For each target, the MSD software computes the lower limit of detection (LLOD) as 2.5 standard deviations above the blank.

Given that BACE1 can directly cleave longer Aβ species between Leu34 and Met35 in vitro (FIG. 1), it was hypothesized that Aβ degradation would be affected by altered BACE1 expression levels in vivo via the Aβ34 pathway. To test this, endogenous cerebral BACE1, APP, and Aβ levels were analyzed from BACE1−/− and BACE1+/− mice, as well as their wild type (BACE1+/+) littermates (FIGS. 2a-g). BACE1 protein levels in the brain of BACE1+/− mice were approximately half that of wild type mice, as analyzed by Western blot (FIGS. 2a and b). Furthermore, BACE1−/− mice had significantly elevated levels of cerebral APP and/or sAPP compared to their BACE1+/− and wild type littermates, while there was no significant difference between BACE1+/− and wild type animals (FIGS. 2a and c). Notably, the former is possibly due to increased levels of full-length APP.

Figure 3:
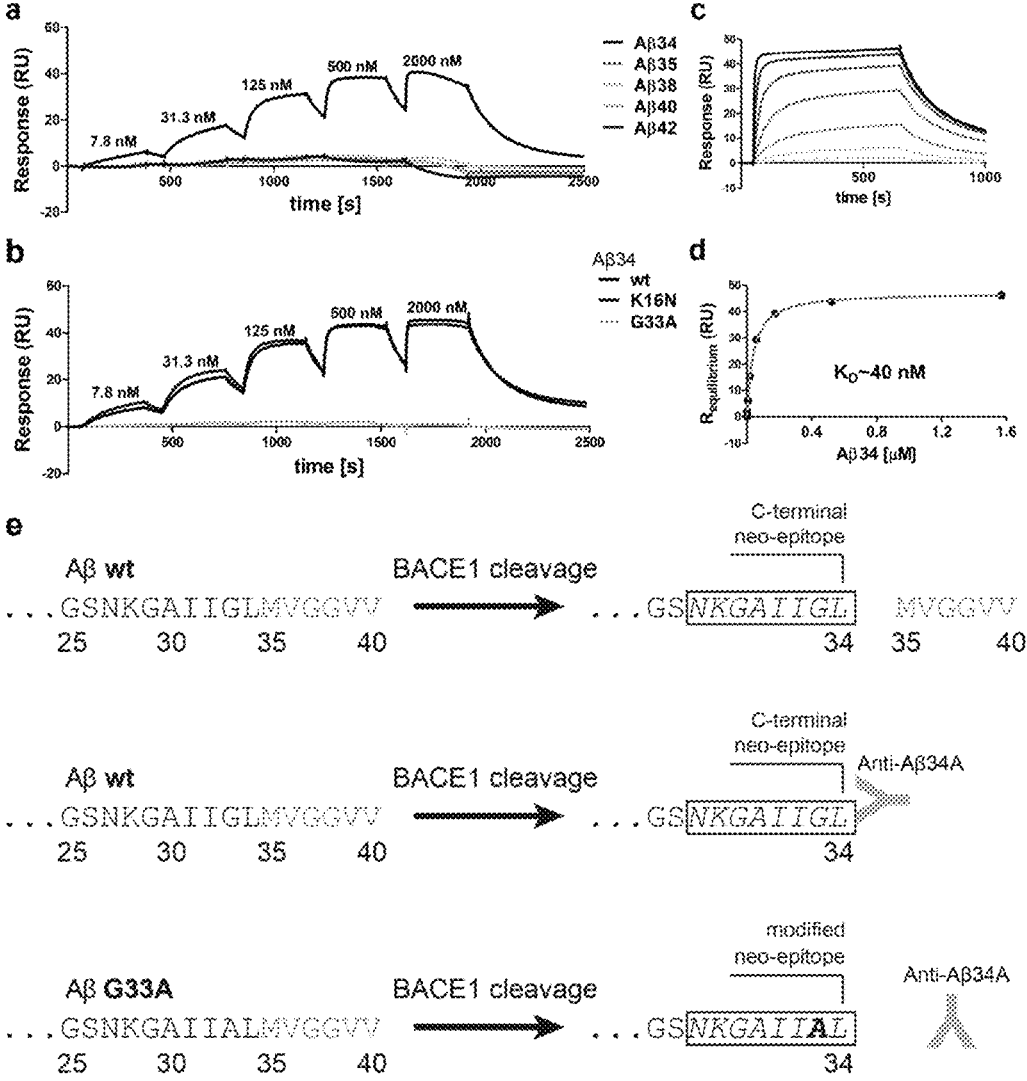
FIG. 3 illustrates the characterization of high-affinity, neo-epitope antibody against Aβ34, as assessed by surface plasmon resonance (SPR) showing in (a) representative single-cycle SPR to demonstrate the specificity and kinetics of synthetic Aβ peptides binding to immobilized anti-Aβ34 antibody (i.e. mab34 captured to anti-Fc sensor); in (b) representative single-cycle SPR to demonstrate the specificity and kinetics of synthetic Aβ34 peptide variants binding to mab34 captured to anti-Fc sensor; in (c and d) representative multi-cycle SPR demonstrates saturable, dose-dependent binding of Aβ34 peptide (0-1.6 UM; 3-fold dilution series, lightest to darkest) to immobilize anti-Aβ34 antibody; steady-state amounts of Aβ34 bound ($R_{equilibrium}$) were plotted as a function of concentration (symbols, raw data) and then subjected to non-linear regression analysis (line, curve fitting) to determine the apparent equilibrium dissociation constant ($K_D$); and in (e) cleavage between L34 and M35, e.g. by BACE1, generates the C-terminal neo-epitope, which is specifically recognized by mab34 whereas the G33A modified neo-epitope is not recognized by mab34.
Figure 4:
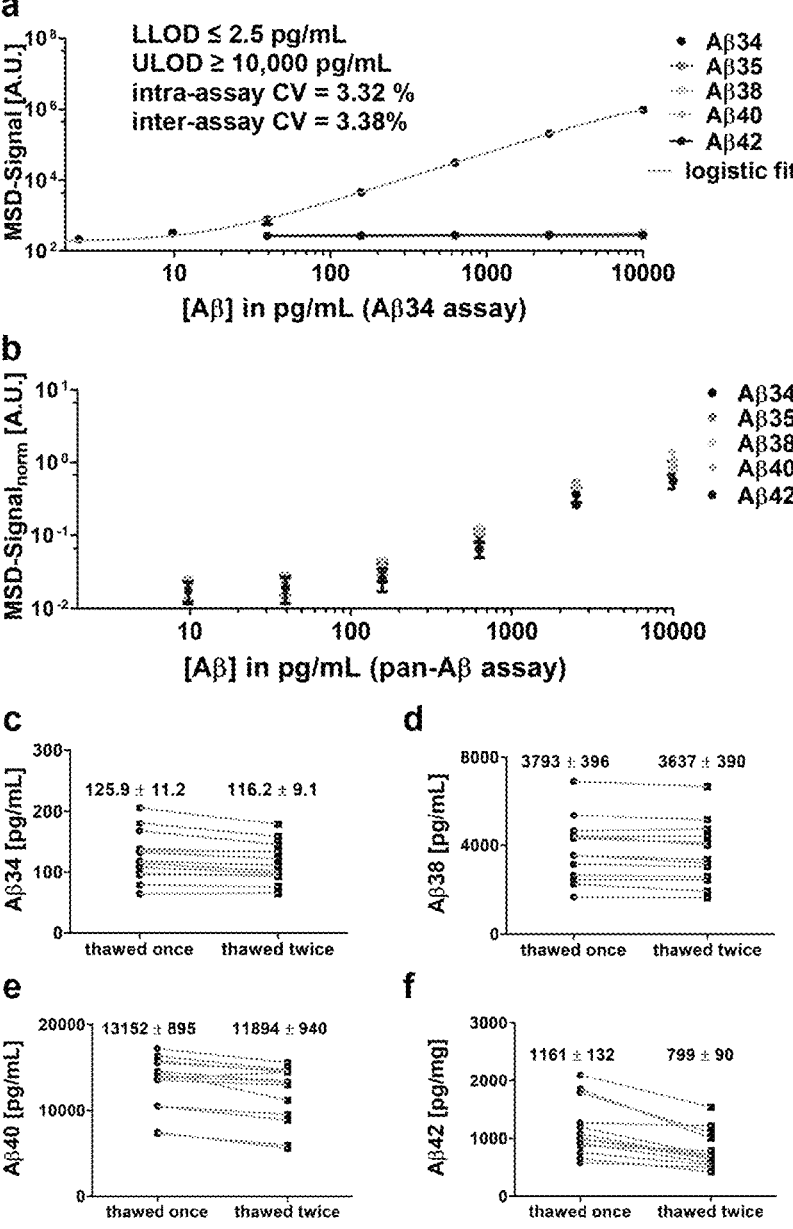
FIG. 4 illustrates the development of an ultrasensitive Meso Scale Discovery (MSD) multiplexing assay for the novel quantification of Aβ34 showing in (a) based on the monoclonal neo-epitope specific mab34, an ultra-sensitive, electrochemiluminescence-based immunoassay was developed using MSD technology, wherein the assay was specific for Aβ34 without any significant cross-reactivity against Aβ35, Aβ38, Aβ40, or Aβ42 (n=3, data points for Aβ35, Aβ38, and Aβ40 are overlaid by Aβ42), measures of assay performance are summarized in the top left corner (n=7). In (b) based on the monoclonal anti-Aβ mid-domain (residues 17-24) antibody 4G8, the response of Aβ34, Aβ35, Aβ38, Aβ40, or Aβ42 (n=4) was tested in a pan-Aβ electrochemiluminescence-based assay. Data were analyzed with a 2-WAY ANOVA. While Aβ concentration showed a significant effect $F_{(5,91)}=57.98$ $p<0.0001$, there was neither a significant effect for Aβ species $F_{(4,91)}=1.57$ $p=0.19$ nor a significant interaction $F_{(20,91)}=0.73$, $p=0.78$. In (c-f) using custom-printed MSD 4-plex plates (for Aβ34, Aβ38, Aβ40, and Aβ42), the effect of thawing cycles on the Aβ quantification was tested. Measured concentrations of Aβ34 (c), Aβ38 (d), Aβ40 (e), and Aβ42 (f) from CSF samples that were thawed only once or thawed twice (n=15 CSF samples). The mean concentration±s.e.m. is displayed above the data points.

The endogenous levels of Aβ34, Aβ38, Aβ40, and Aβ42 peptides were measured in the brains of these same mice using a custom 4-plex Meso Scale Discovery (MSD) multiplexing assay (FIGS. 3 and 4). In agreement with previous findings in mice and rats, Aβ38, Aβ40, and Aβ42 were significantly decreased in BACE1−/− mouse brains while their levels did not differ significantly between BACE1+/− and wild type littermates (FIGS. 2e-g). As expected for a fragment generated by BACE1 activity, cerebral Aβ34 levels were decreased in BACE1−/− mice compared with BACE1+/− (FIG. 2d). Notably, Aβ34 levels were also significantly lower in BACE1+/− mice compared with wild type littermates. Apparently, the cerebral amyloidogenic processing of endogenous APP by BACE1 is not impaired by a 50% decreased enzyme availability, since it is indistinguishable in heterozygous knockouts and wild-type littermates (FIG. 2e-g). Furthermore, the Aβ34/Aβ38, Aβ34/Aβ40, and Aβ34/Aβ42 ratios revealed a step-wise decrease with decreasing BACE1 levels (FIGS. 2h and j). These findings support the concept that cerebral BACE1 levels are limiting for its amyloidolytic activity in vivo relying on conversion of the longer Aβ species to Aβ34, while BACE1 levels are not limiting for APP cleavage resulting in Aβ38, Aβ40, and Aβ42.

Wild type rats were treated with the BACE1-specific inhibitor MK-8931. The inhibitor had no effect on cerebral APP and/or sAPP levels (FIGS. 5a and b). Cerebral Aβ34 levels were significantly decreased in rats treated with concentrations of 1 and 20 mg/kg (FIG. 5c). In contrast, cerebral Aβ40 and Aβ42 levels were only decreased in the 20 mg/kg but not the 1 mg/kg cohort (FIGS. 5d and e). Consequently, the ratios Aβ34/Aβ40 and Aβ34/Aβ42 were found significantly decreased at 1 and 20 mg/kg (FIGS. 5f and g). In agreement with findings in BACE1+/− mice, these results indicate that cerebral Aβ34 levels are more sensitive to changes in BACE1 activity than the longer Aβ species.

Figure 5:
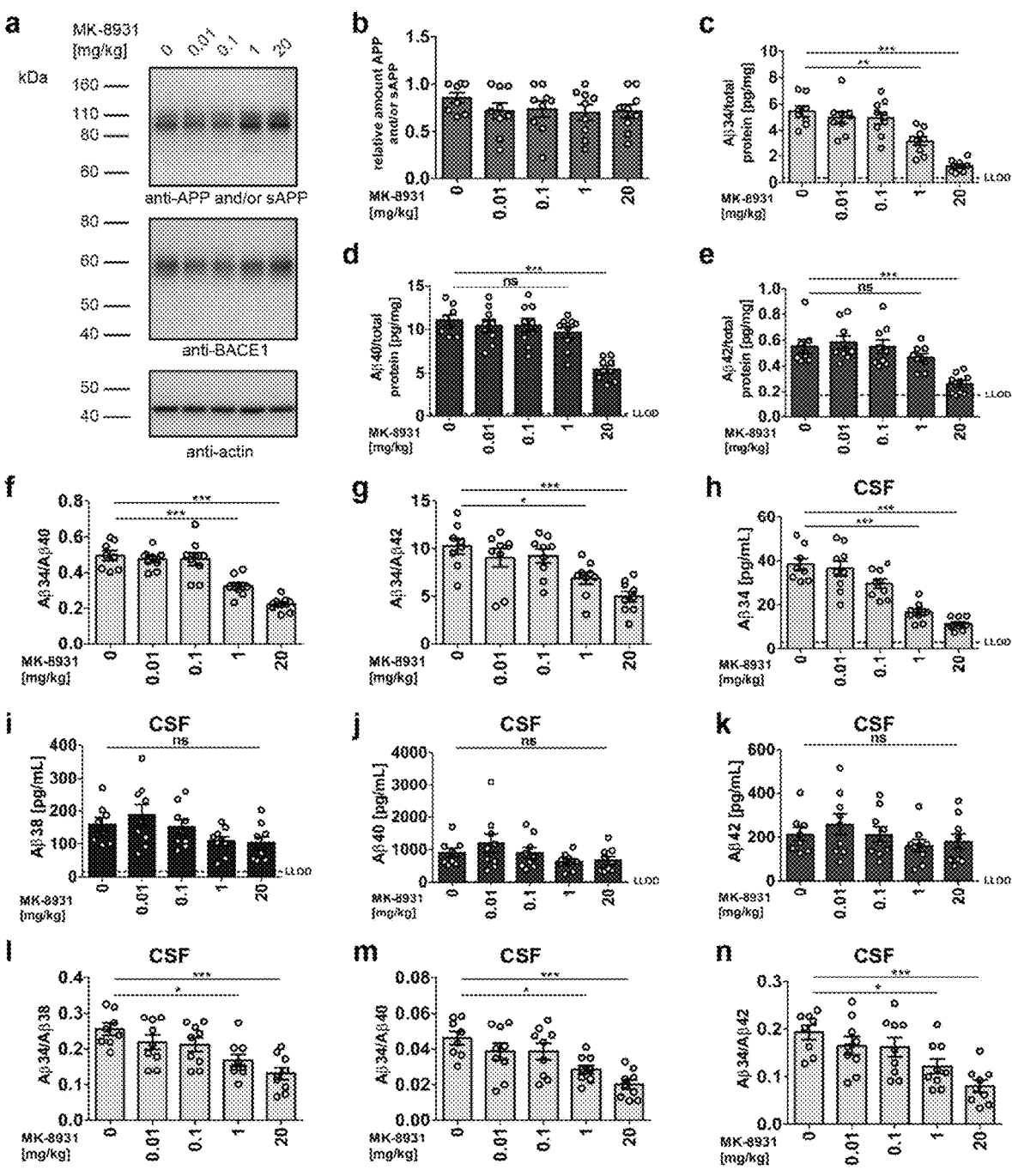
FIG. 5 illustrates the pharmacological inhibition of Aβ34 generation in rats, showing endogenous levels of APP and/or sAPP, BACE1, and Aβ in rats 1 h after intravenous injection of the indicated concentrations (mg/kg) of the BACE1-specific inhibitor (MK-8931), wherein it is shown western blot of endogenous APP and/or sAPP and BACE1 expression in (a) and corresponding quantification of relative protein amounts of APP and/or sAPP in (b). Quantification (pg/mg total protein) of absolute amounts of Aβ34 in (c), Aβ40 in (d), and Aβ42 in (e) are shown as determined by custom MSD multiplexing assays. Ratios of Aβ34/Aβ40 in (f) and Aβ34/Aβ2 in (g) are displayed. Quantification of CSF levels of Aβ34 in (h), Aβ38 in (i), Aβ40 in (j), and Aβ42 in (k) as well as display of the ratios Aβ34/Aβ38 in (l), Aβ34/Aβ40 in (m), and Aβ34/Aβ42 in (n). Statistics: (b) 1-WAY ANOVA, $F_{(4,39)}=0.63$, $p>0.05$, (c) 1-WAY ANOVA, $F_{(4,39)}=22.40$, $p<0.0001$, (d) 1-WAY ANOVA, $F_{(4,39)}=12.81$, $p<0.0001$, (e) 1-WAY ANOVA, $F_{(4,39)}=9.38$, $p<0.0001$, (f) 1-WAY ANOVA, $F_{(4,39)}=25.93$, $p<0.0001$, (g) 1-WAY ANOVA, $F_{(4,39)}=8.02$, $p<0.0001$, (h) 1-WAY ANOVA, $F_{(4,39)}=26.55$, $p<0.0001$, (i) 1-WAY ANOVA, $F_{(4,39)}=2.69$, $p<0.05$, (j) 1-WAY ANOVA, $F_{(4,39)}=1.71$, $p<0.05$, (k) 1-WAY ANOVA, $F_{(4,39)}=1.09$, $p>0.05$, (l) 1-WAY ANOVA, $F_{(4,39)}=6.87$, $p<0.001$, (m) 1-WAY ANOVA, $F_{(4,39)}=7.36$, $p<0.001$, (n) 1-WAY ANOVA, $F_{(4,39)}=6.74$, $p<0.001$. Bars and error bars indicate mean±s.e.m. Tukey's post-hoc tests were performed for pairwise comparisons; selected comparisons are highlighted *$p<0.001$, $p<0.01$, *$p<0.05$, ns=non-significant $p>0.05$.

Aβ34, Aβ38, Aβ40, and Aβ42 levels were measured in the CSF of these rats. CSF-Aβ34 levels were significantly decreased in the cohorts treated with 1 and 20 mg/kg (FIG. 5h), however there was no change for Aβ38, Aβ40, and Aβ42 (FIGS. 5i and k). Furthermore, the ratios Aβ34/Aβ38, Aβ34/Aβ40, and Aβ34/Aβ42 in CSF were significantly decreased in the animals treated with 1 and 20 mg/kg (FIGS. 5l and n). Overall, the results of these experiments demonstrate that the pharmacological inhibition of BACE1 differentially affects the amyloidogenic activity, and the amyloidolytic activity of the enzyme in vivo. Importantly, the latter seems more sensitive than the former to the amount of enzyme present (FIG. 2) and BACE1 activity (FIG. 5).

Figure 6:
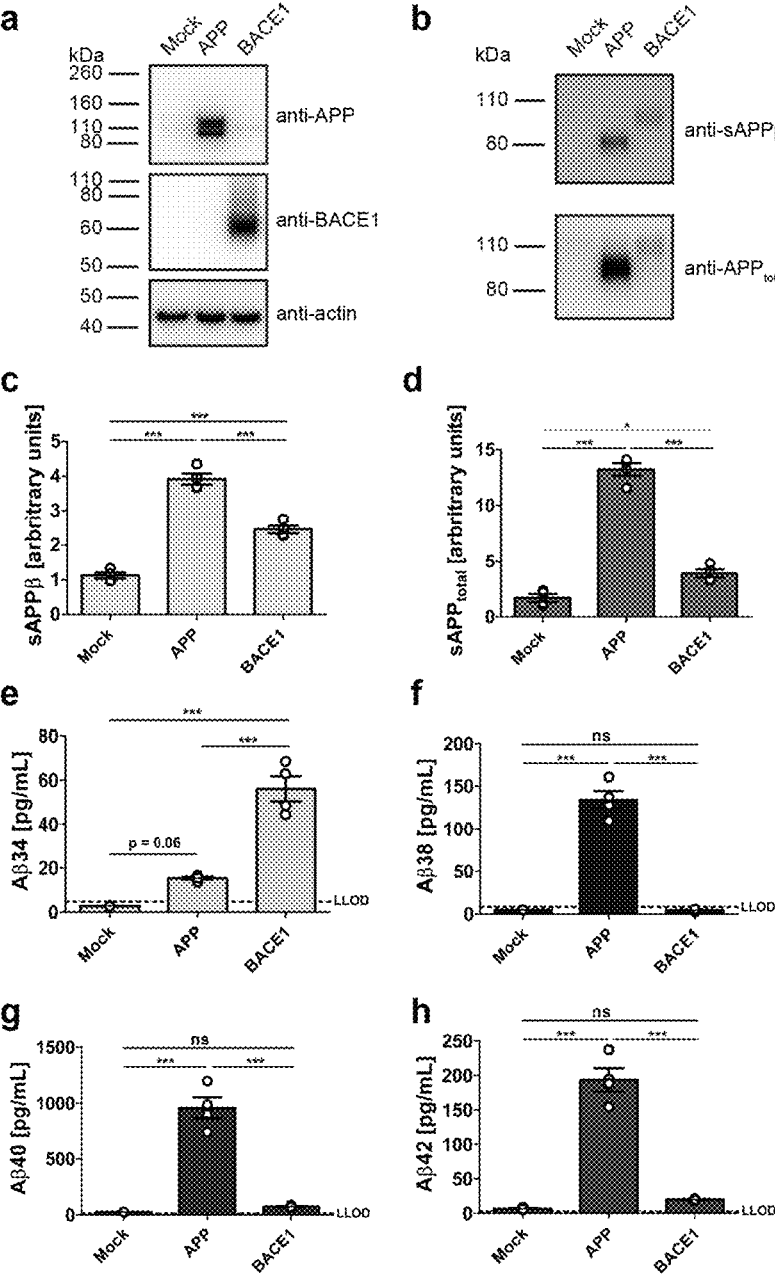
FIG. 6 illustrates surplus of either APP or BACE1 differentially affect APP processing, wherein using SH-SY5Y cells stably expressing APP695 or BACE1, cleavage of APP was analyzed by Western blot and ultra-sensitive MSD assay. Representative Western blots for the examination of APP, BACE1, sAPPβ, and SAPP total (a, b), and the corresponding quantification for the relative amounts of sAPPβ (c) and sAPP_total (d). MSD multiplexing to quantify the absolute amounts of Aβ34 (e), Aβ38 (f), Aβ40 (g), and Aβ42 (h). Data were collected from 4 independent experiments. Bars and error bars indicate mean±s.e.m. (c-h). Data were analyzed with 1-WAY ANOVAs and Tukey's post-hoc tests were performed for pairwise comparisons. (c) SAPPβ, $F_{(2,9)}=131.2$, $p<0.0001$, (d) sAPP_total, $F_{(2,9)}=190.3$, $p<0.0001$, (e) Aβ34, $F_{(2,9)}=70.04$, $p<0.0001$, (f) Aβ38, $F_{(2,9)}=149.0$, $p<0.0001$, (g) Aβ40, $F_{(2,9)}=89.96$, $p<0.0001$, (h) Aβ42, $F_{(2,9)}=113.6$, $p<0.0001$.

It was then tested whether Aβ34 levels would be affected by either a surplus of substrate or enzyme in a human neuronal cell type. Using human neuroblastoma (SH-SY5Y) cells stably overexpressing APP or BACE1 (FIG. 6a), secreted levels of Aβ34, Aβ38, Aβ40, and Aβ42 were measured in the supernatants using the ultra-sensitive 4-plex assay, whereas sAPPβ and sAPP$_{total}$ were detected by Western blot (FIGS. 6a-h). Overexpression of APP mildly increased Aβ34 levels (not statistically different from empty plasmid (Mock)-transfected cells, p=0.06) and significantly elevated sAPPβ, sAPP$_{total}$, Aβ38, Aβ40, and Aβ42, as compared with Mock-transfected cells (FIGS. 6b-h). Conversely, in BACE1 overexpressing cells, Aβ34 levels were significantly elevated approximately three-fold compared with APP-overexpressing conditions, while Aβ38, Aβ40, and Aβ42 levels showed only a mild trend toward elevation compared with the control (FIGS. 6e and h). Furthermore, more APP was shed from either of these cell lines (FIGS. 6c and d). The apparent molecular weights of endogenous APP and sAPPs are slightly higher than those from APP695 transfected cells (FIGS. 3a and b), which is likely due to the fact that undifferentiated SH-SY5Y cells express not only APP695 but also splice variants with KPI- and OX-2 domains. Overall, a surplus of either substrate or enzyme affects APP processing differentially in the human neuronal cell line, resulting in (i) increased Aβ38, Aβ40, and Aβ42 release from APP overexpressing cells, or (ii) an enhanced degradation of all longer Aβ forms into Aβ34 in BACE1 overexpressing cells.

Figure 7:
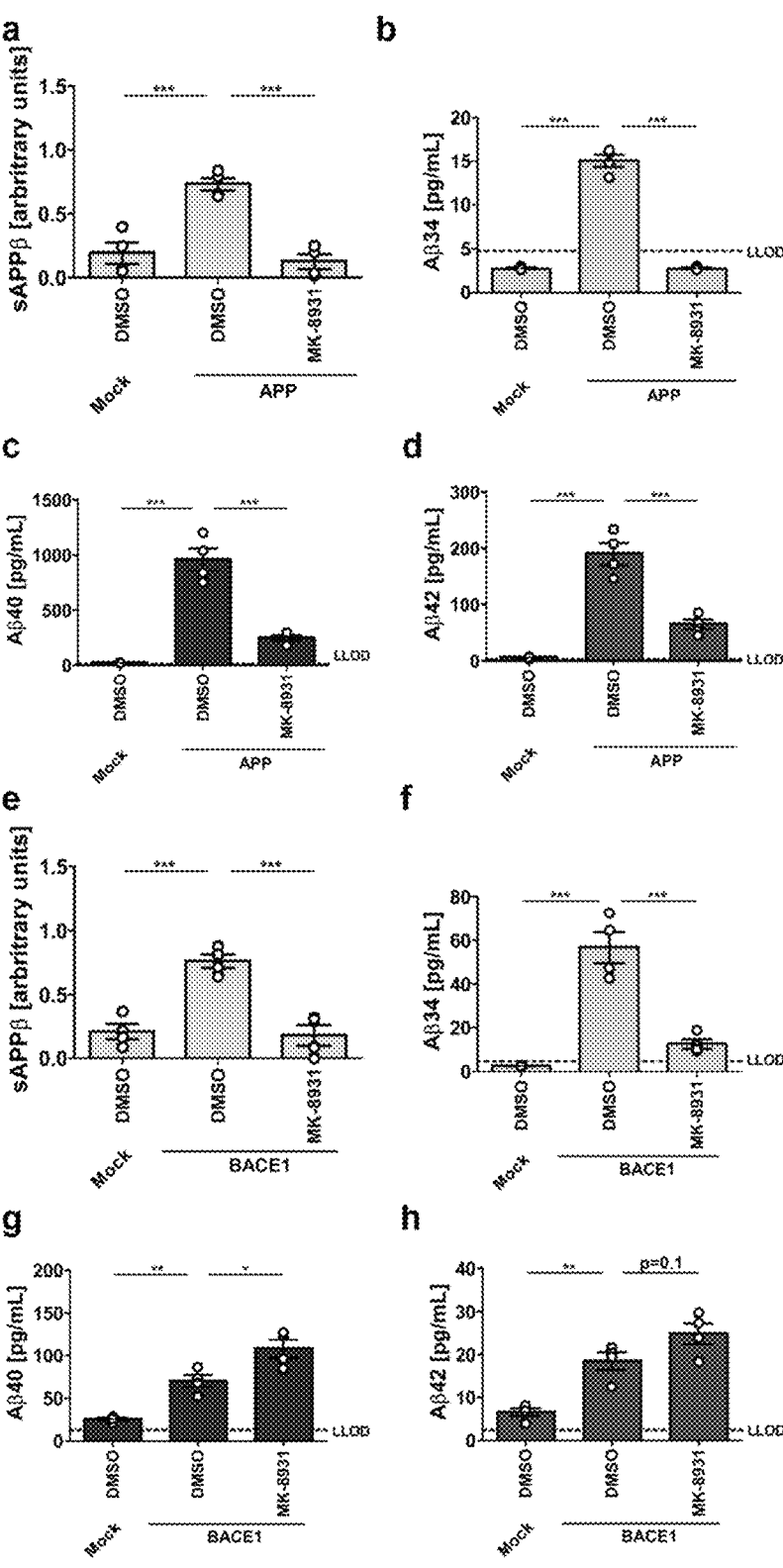
FIG. 7 illustrates surplus of either APP or BACE1 differentially affect BACE1 inhibition, showing cleavage of APP was analyzed by Western blot and ultra-sensitive MSD assays. Absolute or relative amounts of products were quantified from SH-SY5Y cells stably expressing APP695 (a-d) or BACE1 (e-h) quantification of relative amounts of sAPPβ (a, e), and absolute amounts of Aβ34 (b, f), Aβ40 (c, g), and Aβ42 (d, h). Data were collected from 4 independent experiments. Bars and error bars indicate mean±s.e.m. Tukey's post-hoc tests were performed for pairwise comparisons; selected comparisons are highlighted *$p<0.001$, $p<0.01$, *$p<0.05$, ns=non-significant $p>0.05$. (a) sAPPβ, 1-WAY ANOVA, $F_{(2,9)}=26.6$, $p<0.001$, (b) Aβ34, 1-WAY ANOVA, $F_{(2,9)}=296.1$, $p<0.0001$, (c) Aβ40, 1-WAY ANOVA, $F_{(2,9)}=65.9$, $p<0.0001$, (d) Aβ42, 1-WAY ANOVA, $F_{(2,9)}=59.4$, $p<0.0001$, (e) sAPPβ, 1-WAY ANOVA, $F_{(2,9)}=25.4$, $p<0.001$, (f) Aβ34, 1-WAY ANOVA, $F_{(2,9)}=45.3$, $p<0.0001$, (g) Aβ40, 1-WAY ANOVA, $F_{(2,9)}=30.8$, $p<0.0001$, (h) Aβ42, 1-WAY ANOVA, $F_{(2,9)}=23.3$, $p<0.001$.
Figure 8:
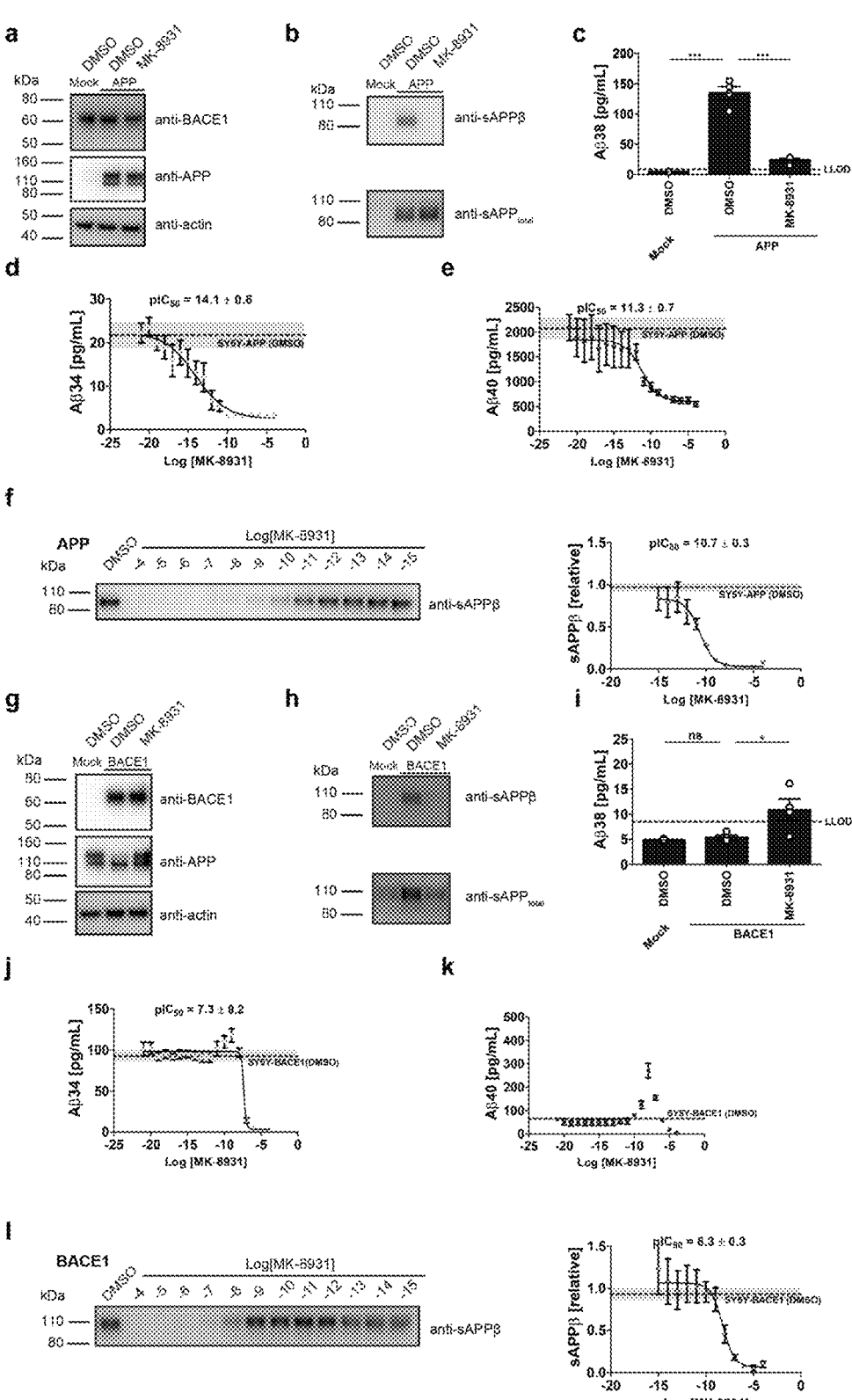
FIG. 8 illustrates pharmacological BACE1 inhibition at high substrate and high enzyme levels showing representative Western blots for the examination of APP, BACE1, sAPPβ, and sAPP_total in APP (a-f) or BACE1 (g-l) overexpressing SH-SY5Y cells treated with vehicle (DMSO) or BACE1 inhibitor (MK-8931). (c and i) MSD multiplexing to quantify the absolute amounts of Aβ38. Data were collected from 4 independent experiments. Bars and error bars indicate mean±s.e.m. (c, i) Data were analyzed with 1-WAY ANOVAs and Tukey's post-hoc tests were performed for pairwise comparisons. (c) Aβ38, $F_{(2,9)}=118.4$, $p<0.0001$, (i) Aβ38, $F_{(2,9)}=6.8$, $p<0.05$. (d-f,j-l) Quantification of relative amounts of sAPPβ, including representative Western blots (f, l), and absolute amounts of Aβ34 (d, j) and Aβ40 (e, k). Data were collected from 4 independent experiments. Circles and error bars or dashed line with grey shaded area indicate mean±s.e.m. Dose-inhibition curves were fit with variable slope equations (four parameter model). Above graph $-\log_{10}(IC_{50})=pIC_{50}\pm$s.e.m are displayed.

To investigate whether BACE1 inhibition differentially affects the Aβ profiles, SH-SY5Y cells overexpressing APP or BACE1 were treated with MK-8931 at approximately 20-fold of its published IC$_{50}$ (i.e. [MK-8931]=100 nM, FIGS. 7 and 8). Conditioned medium from APP overexpressing SH-SY5Y cells showed significantly decreased levels of sAPPβ, Aβ34, Aβ38, Aβ40, and Aβ42 in the presence of MK-8931 (FIGS. 7a-d and 8a-c). Furthermore, a dose-inhibition curve for MK-8931 was performed and sAPPβ (Western blot), Aβ34 (MSD 1-plex), and Aβ40 (MSD 1-plex) were measured (FIGS. 8d-f). In APP overexpressing SH-SY5Y cells, MK-8931 dose-dependently decreased sAPPβ (pIC$_{50}$=10.7±0.3), Aβ34 (pIC$_{50}$=14.1±0.6), and Aβ40 levels (pIC$_{50}$=11.3±0.7) (FIGS. 7d-f). In contrast, in conditioned medium from BACE1 overexpressing SH-SY5Y cells, only the levels of sAPPβ and Aβ34 were significantly decreased in the presence of the inhibitor (FIGS. 7e, f, 8g and h), while Aβ38 and Aβ40 were significantly increased and Aβ42 levels showed a trend for being elevated, p=0.1 (FIG. 7 g and h, and FIG. 8i). The dose-inhibition curve in BACE1 overexpressing SH-SY5Y cells, revealed that MK-8931 only dose-dependently decreased sAPPβ (pIC$_{50}$=8.3±0.3) and Aβ34 levels (pIC$_{50}$=7.3±0.2) (FIGS. 8j and l). Interestingly, Aβ40 levels were decreased at high inhibitor concentrations (p[MK- 8931]>−6), elevated at intermediate concentrations (−10<p [MK-8931]<−6) and unchanged at low concentrations (−10>p[MK-8931]) (FIG. 8k). Ultimately, the results of these experiments show that the response to pharmacological BACE1 inhibition depends on the relative abundances of BACE1 and its substrate APP. Notably, inhibition with insufficient amounts of compound at high levels of BACE1 could result in undesired elevated Aβ40 and Aβ42 levels. However, BACE1 inhibitor doses used in vivo can effectively reduce the levels of longer Aβ species.

Figure 9:
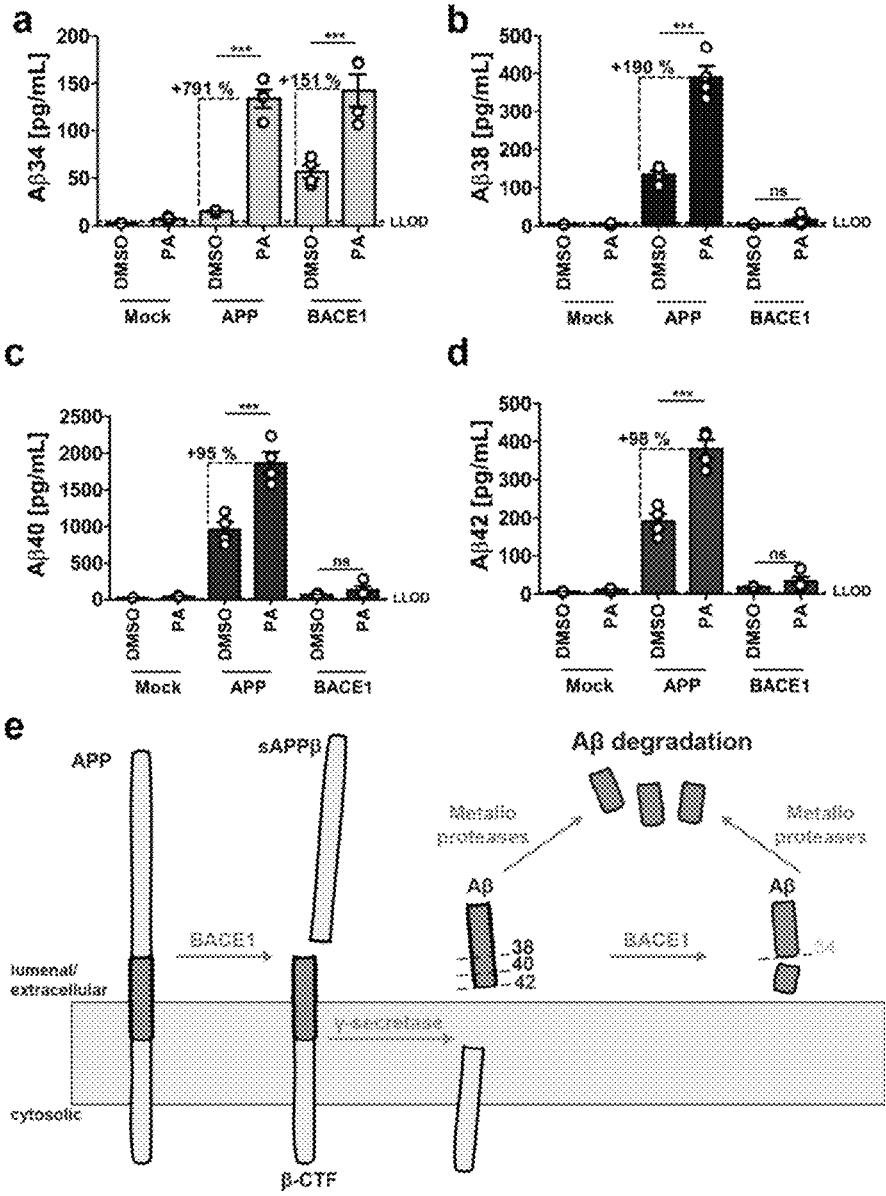
FIG. 9 illustrates attenuation of Aβ34 degradation in the presence of metalloprotease inhibitors wherein using SH-SY5Y cells stably expressing APP695 or BACE1, MSD multiplexing to quantify the absolute amounts of Aβ34 (a), Aβ38 (b), Aβ40 (c), and Aβ42 (d) was performed. Data were collected from 4 independent experiments. Bars and error bars indicate mean±s.e.m. Data were analyzed with 2-WAY ANOVAs and significant interactions were followed up with simple main effects treatment. *$p<0.001$, $p<0.01$, *$p<0.05$, ns=non-significant $p>0.05$. (a) Aβ34, interaction $F_{(2,18)}=23.93$ $p<0.0001$, simple main effects Mock $F_{(1,18)}=0.12$ $p>0.05$, PP $F_{(1,18)}=97.02$ $p<0.0001$, BACE1 $F_{(1,18)}=50.41$ $p<0.0001$ (b) Aβ38, interaction $F_{(2,18)}=63.26$ $p<0.0001$, simple main effects Mock $F_{(1,18)}=0.002$ $p>0.05$, APP $F_{(1,18)}=197.54$ $p<0.0001$, BACE1 $F_{(1,18)}=0.39$ $p>0.05$ (c) Aβ40, interaction $F_{(2,18)}=25.54$ $p<0.0001$, simple main effects Mock $F_{(1,18)}=0.03$ $p>0.05$, APP $F_{(1,18)}=73.97$ $p<0.0001$, BACE1 $F_{(1,18)}=0.34$ $p>0.05$ (d) Aβ42, interaction $F_{(2,18)}=29.08$ $p<0.0001$, simple main effects Mock $F_{(1,18)}=0.07$ $p>0.05$, APP $F_{(1,18)}=97.47$ $p<0.0001$, BACE1 $F_{(1,18)}=0.67$ $p>0.05$. Schematic model (e) describes the proposed APP and Aβ processing pathways involving BACE1 and metalloproteases.

Aβ degrading enzymes (ADE) include the metalloproteases, a large group of proteases that likely cleave Aβ peptide substrates. In general, ADE-derived fragments are short, soluble, and not prone to aggregate. To investigate how Aβ34, Aβ38, Aβ40, and Aβ42 degradation is affected by metalloproteases, APP- or BACE1-overexpressing SH-SY5Y cells were treated with the metalloprotease inhibitor phosphoramidon (PA). Supernatants were analyzed using the 4-plex MSD assay as before (FIG. 9). In APP-overexpressing cells, PA treatment significantly elevated the levels of all Aβ species measured (FIGS. 9a-d). In the presence of PA, however, Aβ34 was increased approximately 9-fold while the levels of Aβ38, Aβ40, and Aβ42 were only about 2-3-fold higher (FIGS. 9a-d). Accordingly, Aβ34 is more sensitive to metalloprotease-mediated degradation compared to the longer species tested. In BACE1 overexpressing cells, Aβ34 levels were increased by about 2.5-fold in the presence of PA, while Aβ38, Aβ40, and Aβ42 levels were not significantly changed (FIGS. 9a-d). Together, these results suggest that Aβ34 is a stable Aβ degradation intermediate of the amyloid degradation cascade. Thus, in the presence of surplus APP substrate (i.e. a high substrate to enzyme ratio), Aβ38, Aβ40, and Aβ42 are degraded by both metalloproteases and the BACE1-mediated Aβ34 pathway (FIG. 9e). Conversely, in the presence of surplus BACE1 enzyme, longer forms of Aβ are predominantly degraded by BACE1, yielding Aβ34 as a metastable cleavage product (FIG. 9e).

Figure 10:
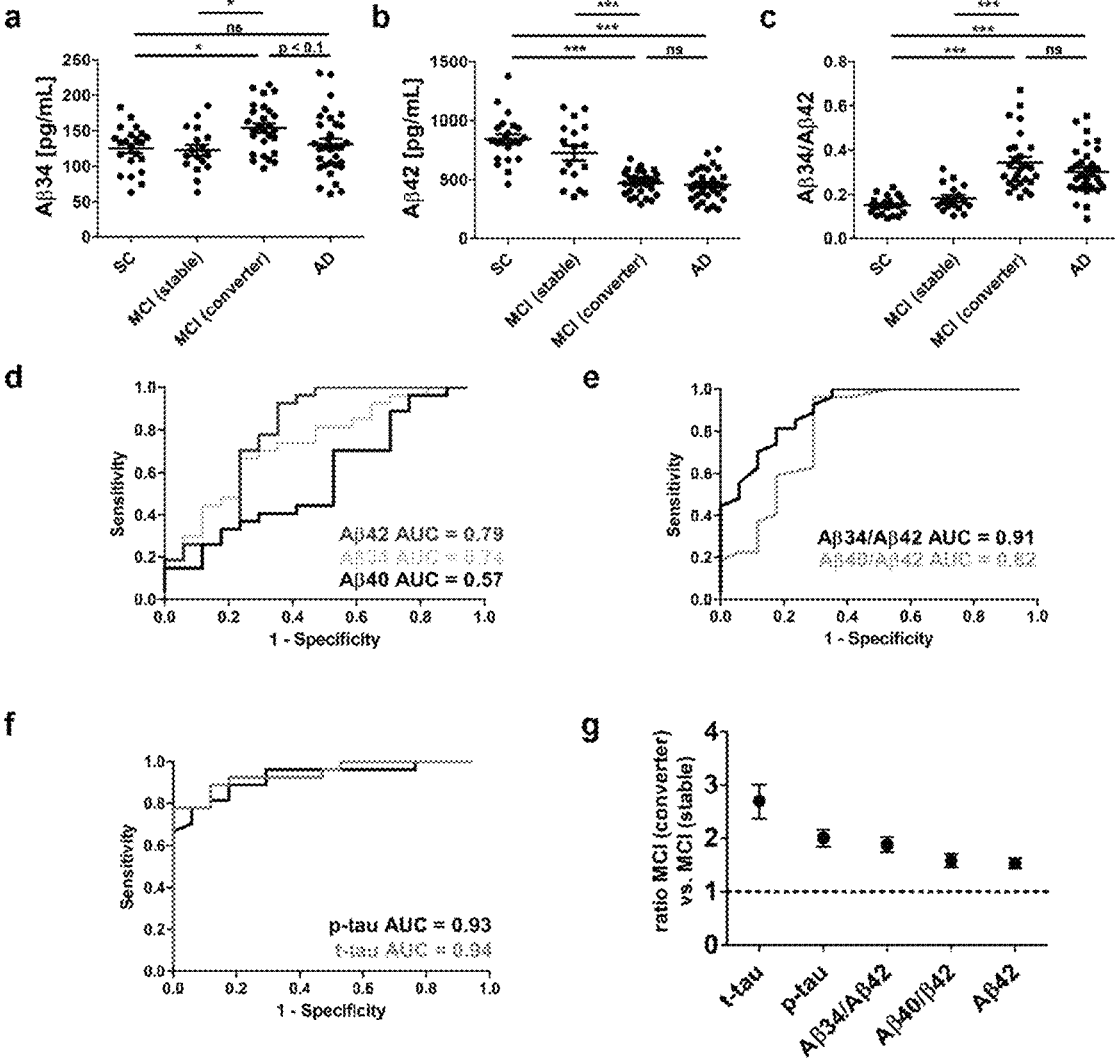
FIG. 10 illustrates the analysis of Aβ34 and core bio-markers in the Amsterdam Dementia Cohort, showing in (a-c) analysis of Aβ34 and Aβ42 in human CSF samples. n=22 subjective complaints (SC), n=17 MCI (stable), n=27 MCI (converter), n=32 Alzheimer's disease (AD). Horizontal lines indicate mean±s.e.m. The data were analyzed with 1-WAY ANOVAs and Tukey's post hoc tests (*p<0.001, p<0.01, *p<0.05, ns p>0.05). (a) Aβ34, 1-WAY ANOVA F(3,94)=3.71, p<0.05, (b) Aβ42, 1-WAY ANOVA F(3,94)= 13.41, p<0.0001, (c) Aβ 34/Aβ42, 1-WAY ANOVA F(3,94)= 21.71, p<0.0001. (d) Receiver operating characteristic (ROC) curves were computed on CSF levels of Aβ34, Aβ40, and Aβ42 in samples from the Amsterdam Dementia Cohort n=17 MCI (stable), n=27 MCI (converter). (e) ROC curves on Aβ40/Aβ42 and Aβ34/Aβ42 ratios from MCI (stable) and MCI (converter)). ROCs were compared using DeLong test: Aβ40/Aβ42 vs. Aβ34/Aβ42 (p=0.0298). (f) ROC curves on p-tau and t-tau from MCI (stable) and MCI (converter)). (g) Comparison of the performance of various molecules measured in CSF, which is based on average MCI (converter) to MCI (stable) ratios in the Amsterdam Dementia Cohort. The MCI (converter) to MCI (stable) ratio of Aβ42 was inverted for better comparison with the other ratios.
Figures 11, 12:
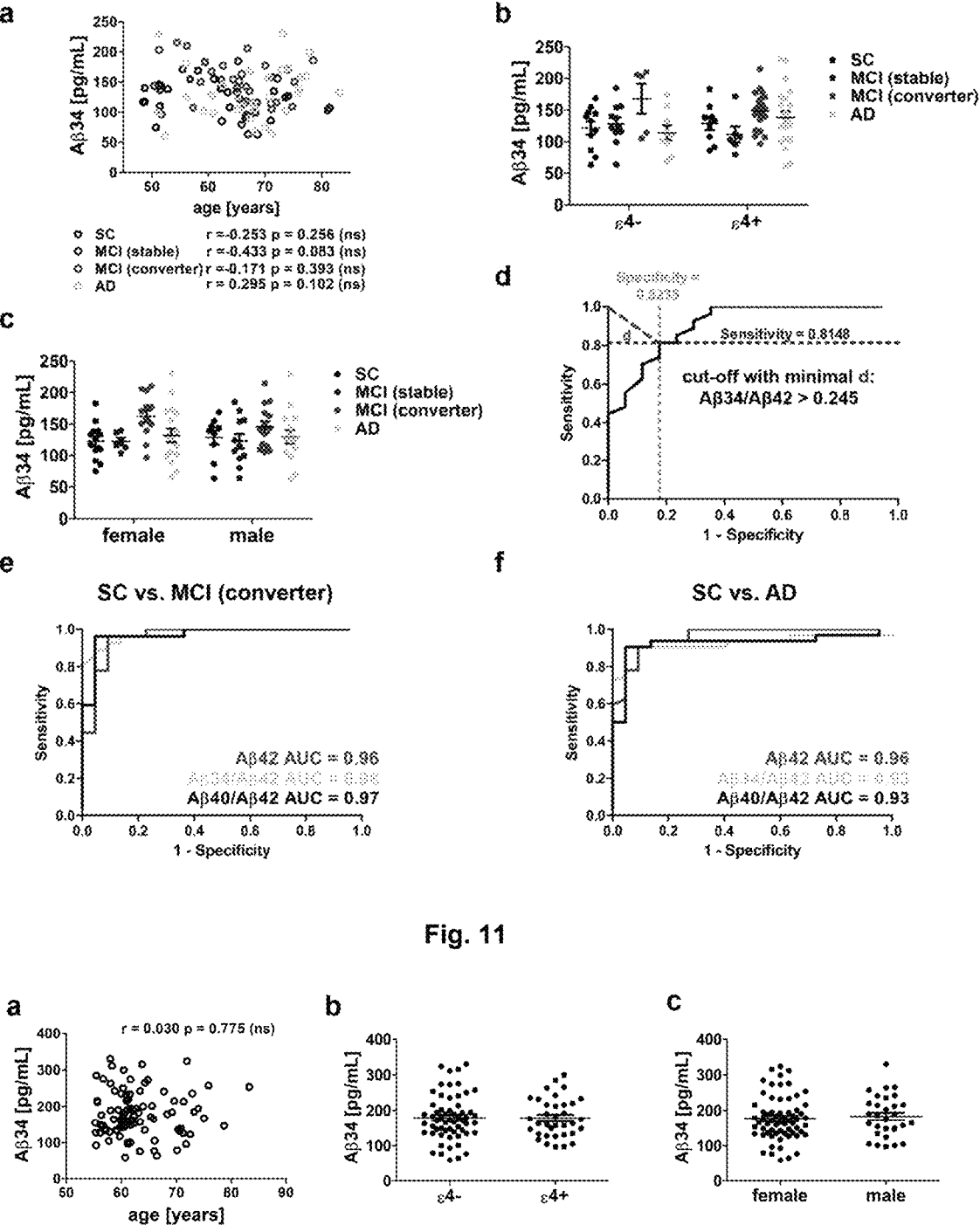
FIG. 11 illustrates the analysis of CSF-Aβ34 in the Amsterdam Dementia Cohort showing in (a) scatterplot of Aβ34 with age. Spearman correlation coefficients (r) were computed to assess the relationship between the variables. (b, c) The effect of ε4 (b) and gender (c) on CSF-Aβ34. The data were analyzed with 2-WAY ANOVAs, (b) ε4 F(1,86)= 0.02, p=0.89; diagnosis F(3,86)=3.70, p=0.02; interaction F(3,86)=1.54, p=0.21 (c) gender F(1,90)=0.15, p=0.70; diagnosis F(3,90)=3.58, p=0.02; interaction F(3,90)=0.41, p=0.74. Horizontal lines indicate mean±s.e.m. (d). The optimal cut-off (point on the ROC curve with the minimum distance (d) to sensitivity=1 and specificity=1) was deter-mined using Pythagoras' theorem and yielded the best cut-off for a ratio >0.245, with a sensitivity of 0.8148 and a specificity of 0.8235. (e, f) ROC curves were computed on CSF levels of Aβ42, Aβ34/Aβ42, Aβ40, and Aβ40/Aβ42 in samples from n=27 MCI (converter) and n=22 SC (e) and n=32 AD and n=22 SC (f).
FIG. 12 illustrates analysis of CSF-Aβ34 in PREVENT-AD showing in (a) scatterplot of Aβ34 with age. Spearman correlation coefficient (r) was computed to assess the rela-tionship between the variables (two-tailed p-value). (b, c) The effect of ε4 (b) and gender (c) on CSF-Aβ34. The data were analyzed with unpaired two-tailed t-tests, (c) 84 t(92)= 0.02, p=0.98; (d) gender t(92)=0.43, p=0.67. Horizontal lines indicate mean±s.e.m.

To explore the associations between Aβ34 and putative changes in BACE1 expression observed in AD, Aβ34 in 98 human CSF samples were analyzed from the Amsterdam Dementia Cohort. Samples were collected from 22 people with subjective cognitive complaints (SC), 17 with MCI that remained stable, 27 with MCI that later progressed to AD dementia (i.e. MCI converters), and 32 AD patients. Using the MSD assay, it was found significantly elevated Aβ34 levels in the CSF of MCI converters when compared to SC or MCI stable (FIG. 10a). Furthermore, the levels in MCI converters showed a trend for being elevated compared to AD patients (the greater variability is likely due to a larger heterogeneity in this group). CSF-Aβ34 levels from all groups did not associate with age, the genetic risk allele APOE 84, or gender (FIGS. 11a-c). As expected, there was a decrease in Aβ42 in AD patients compared with all other groups, as well as reduced Aβ42 levels in MCI converters compared to the SC and MCI stable group (FIG. 10b). These changes are likely due to the sequestration of Aβ42 into amyloid plaques and indicate that MCI converters and AD patients are typically amyloid positive (Aβ+). The Aβ34/Aβ42 ratio is significantly elevated in the MCI converter and AD group compared with the other groups (FIG. 10c).

To assess whether CSF-Aβ34 could provide important new information during the early stages of AD, it was tested whether Aβ34 could discriminate between MCI patients who converted to dementia vs. non-converters from the Amsterdam Dementia Cohort. Receiver operating characteristic (ROC) curves of the CSF analytes were used to determine the accuracy of distinction between the MCI converters (i.e. prodromal AD) vs. stable patients. The area under the curve (AUC) for Aβ34 alone was slightly smaller than for Aβ42 (FIG. 10d). Interestingly, the Aβ34/Aβ42 ratio (AUC=0.91) significantly improved the diagnostic accuracy compared with the classical Aβ40/Aβ42 ratio (AUC=0.82) (FIG. 10e). An optimal cut-off analysis yielded the best cut-off for an Aβ34/Aβ42 ratio >0.245, where sensitivity was 81.48% and specificity 82.35% (FIG. 11d). The improved diagnostic accuracy of the Aβ34/Aβ42 ratio seemed specific for the distinction between MCI converters and stables. Similar AUCs ranging from 0.93 to 0.98 were obtained for Aβ42, Aβ40/Aβ42, and Aβ34/Aβ42 for the distinction between the SC and MCI converters or the SC and AD populations respectively (FIGS. 11e and f). For the distinction between MCI converters and stable patients p-tau and t-tau yielded AUCs of 0.93 and 0.94, respectively (FIG. 10f). To assess how Aβ34/Aβ42 compares to the core AD biomarkers, the ratio between the MCI converter and MCI stable groups were calculated (FIG. 10g). Aβ34/Aβ42 ranked third after the core markers, i.e. total- and phosphorylated-tau but before Aβ40/Aβ42 and Aβ42 (FIG. 10g). Overall, these results suggest that using Aβ34, an indicator for Aβ degradation in combination with Aβ42, a core biomarker for Aβ deposition, can improve the accuracy of prediction compared with Aβ40/Aβ42 regarding MCI patients who will convert to dementia vs non-converters. The Aβ34/Aβ42 ratio could complement but not supplant existing biomarkers, such as CSF-levels of total- and phosphorylated-tau. Nevertheless, this finding suggests that, at certain stages of Aβ34 elevation in the CSF the combination of this marker with reduced Aβ42 may indicate a failure in the clearance pathway associated with AD progression.

To test whether changes in the Aβ34/Aβ42 ratio are already detectable in earlier, pre-symptomatic AD, likely even before signs of neuronal injury become evident, 94 human CSF samples were analyzed from cognitively normal, at-risk individuals from the PREVENT-AD cohort. Individuals enrolled in this study have no diagnosable cognitive dysfunction and are in good general health, but they have a family history of a parent or multiple siblings affected with AD dementia. At enrollment, these individuals were on average 10.2 years younger than the age of dementia onset for their earliest-affected relative. Consistent with earlier Amsterdam Dementia Cohort findings, CSF-Aβ34 levels in the PREVENT-AD samples were not associated with age, APOE 84, or gender (FIGS. 12a-c). It was then tested whether an increased Aβ34/Aβ42 ratio (optimal cut-off Aβ34/Aβ42>0.245; FIG. 10c) could also be observed in cognitively normal individuals from the PREVENT-AD cohort. 17 out of 94 individuals (18.09%) were identified with Aβ34/Aβ42 ratios that were above the estimated cut-off.

Figure 13:
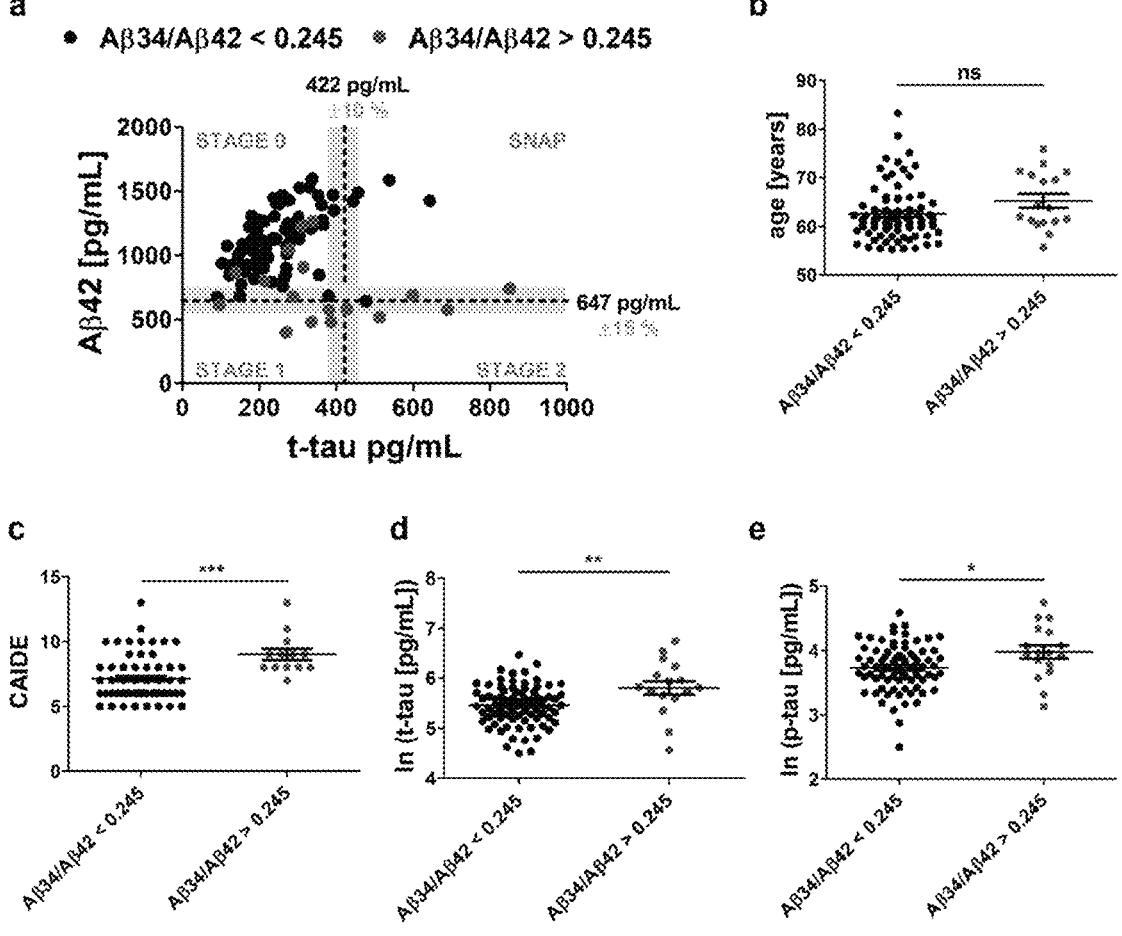
FIG. 13 illustrates the analysis of Aβ34, Aβ42, t-tau, and p-tau in CSF from cognitively normal individuals at risk for Alzheimer's disease, wherein (a-e) PREVENT-AD: analysis of Aβ34, Aβ42, t-tau, and p-tau in CSF samples from cognitively normal individuals at risk for Alzheimer's dis-ease (n=94). (a) Individuals can be separated into stages of pre-symptomatic AD, based on CSF biomarker assessment (t-tau cut-off >422 pg/mL, Aβ42 cut-off≤647 pg/mL, the grey shaded area indicates common inter-assay variances of the used cut-off values). STAGE 0: t-tau and Aβ42 normal; STAGE1: t-tau normal and Aβ42≤647 pg/mL; STAGE 2: t-tau>422 pg/mL and Aβ42≤647 pg/mL; Suspected-non-AD pathology (SNAP): t-tau>422 pg/mL and Aβ42 normal. Individuals with Aβ34/Aβ42 ratio above the optimal cut-off calculated in this study (Aβ34/Aβ42>0.245) are highlighted in magenta. (b-e) Comparison of age, Mann-Whitney U=461.5, p=0.0586 (b); Cardiovascular Risk Factors, Aging, and Incidence of Dementia (CAIDE), Mann-Whit-ney U=184.5, p=0.0004 (c); t-tau, unpaired t-test t(92)= 3.027, p=0.0032 (d); and P$_{181}$-tau (p-tau), unpaired t-test t(92)=2.453, p=0.0168 (e); between individuals with Aβ34/Aβ42 ratios above and below optimal cut-off (*p<0.001, p<0.01, *p<0.05, ns p>0.05). Horizontal lines indicate mean±s.e.m.

The asymptomatic phase of AD is characterized by a sequential appearance of abnormalities, starting with increased cortical Aβ deposition (stage 1), leading to additional signs of neurodegeneration (stage 2; no abnormalities are seen in stage 0). FIG. 13a depicts the Aβ42 and total tau (t-tau) distribution of the PREVENT-AD samples from individuals at different stages of pre-symptomatic AD, with most individuals remaining in the stage 0 group. The horizontal and vertical dotted lines and shaded areas represent Aβ42 and t-tau cut-off values and their inter-assay variances (FIG. 13a). The biomarker assessments (validated CSF-Aβ42 cut-off values including the inter-assay variances) indicated that 15 PREVENT-AD participants are likely candidates having pre-clinical AD at stages 1 and 2 (FIG.

13a). Out of these, 11 presented with Aβ34/Aβ42 ratios above the cut-off (11/15=73.33%) (FIG. 13a). Additionally, 6 out of 73 (8.22%) individuals at stage 0 also showed an elevated Aβ34/Aβ42 ratio. Overall, 37.23% (35/94) of PRE-VENT-AD participants are APOE ε4-carriers. It was noted that APOE 84-carriers were enriched in the group with an elevated Aβ34/Aβ42 ratio (12/17=70.59%). Individuals with elevated Aβ34/Aβ42 were not significantly older (FIG. 13b), but they exhibited significantly increased Cardiovascular Risk Factors, Aging, and Incidence of Dementia scores (CAIDE; FIG. 13c), and significantly increased CSF levels of total- and phosphorylated-tau (t-tau, p-tau; FIGS. 13d and e).

Figure 14:
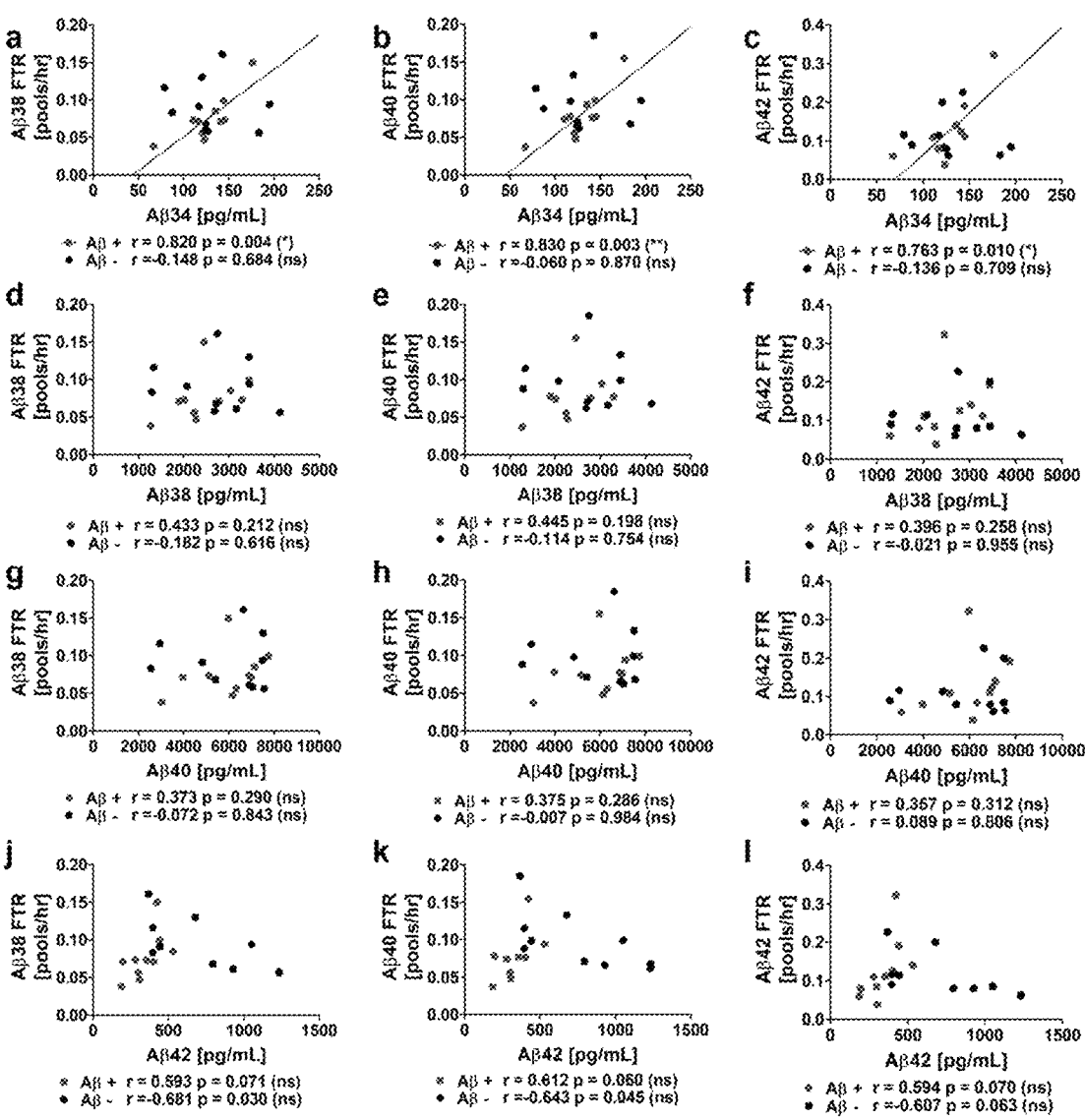
FIG. 14 illustrates that CSF-Aβ34 correlates with the clearance rates of Aβ38, Aβ40, and Aβ42 in amyloid posi-tive individuals, showing analysis of Aβ34, Aβ38, Aβ40, and Aβ42 in human CSF with ultra-sensitive assays (Meso Scale Discovery (MSD)). Aβ38, Aβ40, and Aβ42 clearance (fractional turnover rate, FTR) was previously measured using stable isotope labeling kinetic (SILK). Scatterplots of CSF-Aβ34 (a-c), Aβ38 (d-f), Aβ40 (g-i), or Aβ42 (j-l) with Aβ38 FTR (a, d, g, j), Aβ40 FTR (b, e, h, k), or Aβ42 FTR (c, f, i, l). Pearson correlation coefficients (r) were computed to assess the relationship between the variables. The Bon-ferroni adjusted p-values are: **p<0.003, *p<0.016, ns=non-significant p>0.0125.
Figure 15:
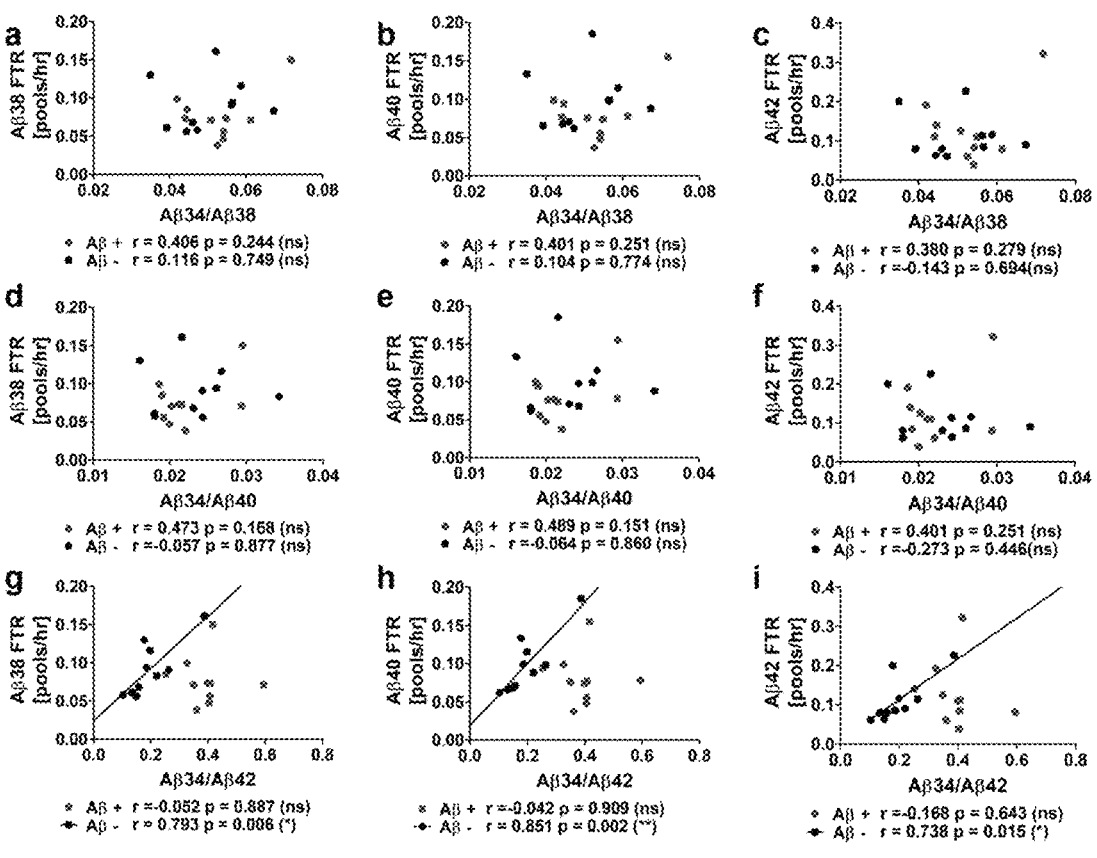
FIG. 15 illustrates that CSF-Aβ34/Aβ42 correlates with the clearance rates of Aβ38, Aβ40, and Aβ42 in amyloid negative individuals, showing analysis of Aβ34, Aβ38, Aβ40, and Aβ42 in human CSF with ultra-sensitive assays (Meso Scale Discovery (MSD)). Aβ38, Aβ40, and Aβ42 clearance (fractional turnover rate, FTR) was previously measured using stable isotope labeling kinetic (SILK). Scat-terplots of CSF-Aβ34/Aβ38 (a-c), Aβ34/Aβ40 (d-f), or Aβ34/Aβ42 (g-i) with Aβ38 FTR (a, d, g), Aβ40 FTR (b, e, h), or Aβ42 FTR (c, f, i). Pearson correlation coefficients (r) were computed to assess the relationship between the vari-ables. The Bonferroni adjusted p-values are: **p<0.003, *p<0.016, ns=non-significant p>0.0125.

In MCI and sporadic AD brain tissue, the levels and enzymatic activity of BACE1 are increased and localized to the surroundings of amyloid deposits. Above, it was described evidence that Aβ34 (an amyloidolytic product of BACE1 activity) is associated with BACE1-mediated Aβ clearance and is elevated in MCI converters, who show evidence of amyloid plaques (Aβ+) (based on their CSF-Aβ42 levels). Thus, the CSF concentrations of Aβ34, Aβ38, Aβ40, and Aβ42 was analyzed in amyloid positive (Aβ+) and amyloid negative (Aβ−) individuals (10 individuals per group; FIG. 14), whose Aβ turnover was previously assessed by stable isotope labeling kinetic (SILK™). It is described that fractional turnover rate (FTR) or true fractional clearance rate, which is associated with the irreversible loss of Aβ38, Aβ40, and Aβ42, showed a significant positive correlation with the CSF-Aβ34 concentrations only in Aβ+ individuals (FIGS. 13a-c). Moreover, the CSF concentrations of Aβ38, Aβ40, and Aβ42 showed no significant correlation with Aβ38, Aβ40, or Aβ42 FTRs in the dataset (FIGS. 13d-i). Interestingly, the ratio Aβ34/Aβ42 correlated with all three FTRs in Aβ−individuals, while the other ratios showed no correlation (FIGS. 15a-i). Overall, the correlation between Aβ34 and the clearance of the longer Aβ species is consistent with earlier results from rodent brains and SH-SY5Y cells, suggesting that elevated BACE1 levels in Aβ+ individuals might shift Aβ38, Aβ40, and Aβ42 into the Aβ34-degradation pathway. In conclusion, Aβ34 might serve as a surrogate marker for the overall clearance of Aβ38, Aβ40, and Aβ42 in Aβ+ and the ratio Aβ34/Aβ42 for the overall clearance of Aβ38, Aβ40, and Aβ42 in Aβ−individuals.

In the Alzheimer's disease field, basic R&D has traditionally focused on the conversion of the amyloid precursor protein into Aβ42 peptides (i.e. aggregating Aβ42) that lead to pathological amyloid plaque deposition in the brain. Clinical R&D has likewise focused on the ratio of Aβ40 to Aβ42 (i.e. soluble Aβ42 decreases in patient CSF as it becomes deposited in plaques) as an indicator of cognitive decline during the clinical progression of AD. In recent years, however, emerging literature now identifies amyloid clearance as an important new paradigm to better understand amyloid imbalances (e.g. synergy between failed clearance and increased deposition) in "sporadic" AD patients.

BACE1 is thought to play a major role in the pathogenesis of AD and several inhibitors have been evaluated in clinical trials for their potential to slow or halt the production of neurotoxic Aβ peptides. In order to attenuate disease progression in individuals with existing amyloid plaques, Aβ production would need to be inhibited by at least 95% since deposition is expected to be fast in Aβ-positive individuals, even at lowered rates of newly produced Aβ. Recently, current treatment approaches have been challenged based upon reports of disappointing results and adverse effects from BACE inhibitor trials.

BACE1 levels are increased in the AD brain, and this could potentially result in increased Aβ production. However, a ~50% reduction in cerebral BACE1 (as reported in BACE1+/− mice and rats) does not alter Aβ38, Aβ40, and Aβ42 levels, suggesting that half the usual amount of BACE1 is sufficient to fully process endogenous APP. Therefore, cerebral BACE1 levels do not appear to be limiting for Aβ38, Aβ40, and Aβ42 production in mice. Furthermore, increased enzyme levels do not lead to an increased amyloid load in the brains of mice overexpressing human BACE1.

Using the newly-developed, high-affinity anti-Aβ34 antibody described herein, it was found that cerebral Aβ34 levels were decreased by about 30% in BACE1+/− mice and by about 40% in wild type rats, 1 h after intravenous injection with 1 mg/kg MK-8931 (with longer Aβ species unaltered). In the CSF of these MK-8931 treated rats, Aβ34 was the only Aβ species that was significantly decreased in the 1 and 20 mg/kg groups. Accordingly, BACE1 is a limiting factor for the amyloidolytic cleavage of longer Aβ species into Aβ34. Furthermore, the data implies that cerebral BACE1 possesses Aβ-degrading properties in vivo, as consistent with an earlier hypothesis based on in vitro studies. The dichotomy between the amyloidogenic and amyloidolytic roles of BACE1 becomes more evident in experimental systems with elevated BACE1 levels. As described herein, for example, it was found that an excess of APP favors amyloidogenic Aβ peptide production, but an excess of BACE1 results in increased Aβ degradation to Aβ34. The characterization provided herein of the BACE1-mediated Aβ34 pathway is consistent with previous findings that cerebral BACE1 is not limiting for Aβ production, observations that until now had remained unexplained due to the lack of understanding about amyloidolytic BACE1 activity.

Since BACE1-derived Aβ34 can be further degraded by PA-sensitive metalloproteases, it may be classified as a metastable intermediate in the degradation cascade of amyloidogenic peptides. The present description show that this process is regulated by BACE1 expression such that when BACE1 may become limiting (i.e. when APP is overexpressed), amyloidogenic Aβ peptides are enzymatically degraded by both metalloproteases and BACE1. However, when BACE1 is present in insufficient or excess amounts (i.e. when overexpressed), the Aβ34 pathway is favored. Since BACE1 is strongly expressed in neurons, particularly at sites of Aβ production in the brain, longer Aβ peptides may be favorably converted into non-toxic Aβ34 at these sites. It is likely that Aβ34 might have a specific biological function and anti-apoptotic actions of this fragment on cultured human cells have been described, however a more thorough characterization is needed in order to determine its physiological role.

Site-specific mutations in APP were found in rare cases of familial early-onset AD (FEOAD) and especially processing at the β-cleavage site of APP could be causally linked to increased and decreased risk of AD. For example, β-cleavage of APP carrying the Swedish mutation is increased (KM670/671NL) and causes FEOAD. In contrast, the Icelandic mutation (A673T) protects against AD, primarily by reducing the β-cleavage of APP as well as modulating Aβ aggregation. In light of the present disclosure, the Icelandic mutation results in reduced Aβ generation, while BACE1-mediated Aβ degradation still occurred. While inhibition of BACE1-mediated cleavage of APP remains an attractive therapeutic approach in AD, it appears that BACE1-mediated blocking of pathogenic Aβ peptide generation alone will not be sufficient to stop plaque growth alone. Furthermore, BACE1 inhibition is likely to affect amyloidolytic cleavage of longer Aβ species into smaller, non-amyloidogenic Aβ34. For this reason, clearance effects was tested in human CSF and, notably, it was found significantly elevated baseline levels of Aβ34 in MCI patients who later progressed to AD. Aβ34 can be detected in human plasma samples (Pannee et al., 2014, Neuroscience Letters, 573:7-12). Furthermore, the Aβ34/Aβ42 ratio significantly improved the diagnostic accuracy to distinguish between prodromal AD and stable MCI compared to the classical Aβ40/Aβ42 ratio. However, elevated CSF-levels of p-tau and t-tau showed the best distinction between the two MCI groups. An elevated Aβ34/Aβ42 ratio in the prodromal stage of AD could indicate that, at early stages of Aβ plaque formation (i.e. decreased CSF-Aβ42 levels), the increased levels and amyloidolytic activity of BACE1 elicit a defense reaction (i.e. increased generation of Aβ34 to facilitate amyloid clearance). While BACE1 levels are elevated around fibrillar Aβ, the fibrillar conformation is resistant against BACE1 cleavage because of its unique structure (under the condition of their co-presence in a cellular compartment with a low pH). Aβ42 fibrils are stabilized by hydrophobic clusters in such a way that they do not grant BACE1 access to the Aβ34 cleavage site. Furthermore, since only Aβ42 turnover (and not Aβ38 or Aβ40) is altered when amyloidosis has started, the surplus of Aβ34 could be mainly derived from Aβ42 since its conformation is different from Aβ38 and Aβ40. Thus, the intracellular Aβ42 can adopt a conformation that is favourable for fibril formation, which makes it especially susceptible to BACE1-mediated degradation at the Aβ34 cleavage site.

Contrary for example to teaching in EP1865326 which discloses a method for the diagnosis of AD based on the determination of the ratio of at least two γ-secretase cleavage products selected from Aβ48, Aβ45. Aβ42, Aβ38 and Aβ35, it is demonstrated herein that the Aβ34/Aβ42 ratio is useful to monitor pre-symptomatic AD, since changes in the classical biomarkers of AD pathogenesis can already be observed before cognitive symptoms appear. In human CSF samples from the PREVENT-AD cohort (i.e. at-risk individuals without current cognitive impairment), it was found that the Aβ34/Aβ42 ratio was elevated, especially in individuals whose biomarker assessment classified them in stages 1 and 2 (signs of cortical Aβ deposition). Overall, few individuals in PREVENT-AD showed reduced CSF-Aβ42 (≤647 pg/mL). In families with autosomal-dominant AD, reduced CSF-Aβ42 and increased tau in asymptomatic mutation carriers were already detected 10 to 20 years before the estimated age of onset. At present, members of the PREVENT-AD cohort tend to be several years younger compared to the onset of dementia in their affected relative(s) and, in contrast to mutation carriers, they probably vary substantially in their degree of progression of pre-symptomatic AD. Interestingly, individuals in stage 0 with an elevated Aβ34/Aβ42 ratio were identified.

Consistent with the concept of amyloid clearance and deposition mechanisms indicating failed clearance in pre-symptomatic stages of AD, it was found that the Aβ34 levels in CSF correlate with the overall clearance rates of Aβ38, Aβ40, and Aβ42 in Aβ+ but not Aβ-individuals. In contrast, the CSF Aβ34/Aβ42 ratios correlate with the overall clearance rates of Aβ38, Aβ40, and Aβ42 in Aβ- but not Aβ+ individuals. Since inter-individual variances in Aβ clearance rates are affected by various factors including age, genetics, or pathological processes, it is rather unlikely that the levels of an individual protein, such as BACE1, could determine the overall Aβ clearance from the brain. However, the findings provided herein suggest that under pathological conditions, elevated BACE1 levels in the brain direct a large proportion of Aβ38, Aβ40, and Aβ42 into BACE1-mediated Aβ clearance via the Aβ34 degradation pathway. Given this, Aβ34 might be used as a marker for the overall clearance of these peptides in Aβ+ individuals.

Thus, under non-pathological conditions, a special relationship exists between Aβ34 and Aβ42, which explain the correlation of their ratio with the overall Aβ clearance. Once Aβ42 gets deposited in plaques the correlation with clearance is lost, likely due to an altered Aβ42 degradation. Under these circumstances, Aβ34 alone becomes the predictor of clearance rates.

Figure 16:
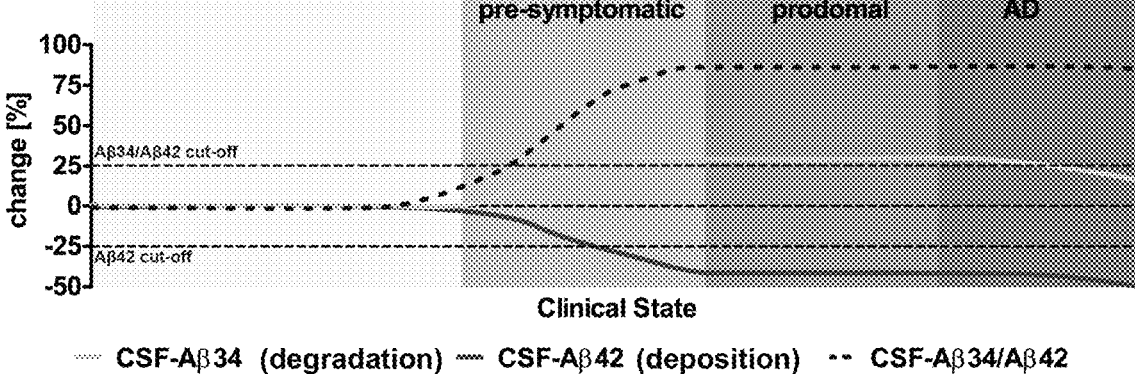
FIG. 16 illustrates the conceptual model of CSF-Aβ34, -Aβ42, and -Aβ34/Aβ42 changes throughout the various clinical stages of Alzheimer's disease (AD). Before a clini-cal diagnosis of Alzheimer's disease (AD), decades of Aβ peptide deposition lead to plaque formation in pre-symp-tomatic and prodromal stages of the disease. Incorporating Aβ34 (marker of enzymatic Aβ degradation) with measures of Aβ42 (marker for cerebral Aβ deposition) complements current biomarker assessments and provide additional infor-mation about Aβ turnover.

In summary, it is described herein that, in vivo, BACE1 is limiting for the degradation of longer Aβ peptides into the intermediate Aβ34. The levels of this amyloidolytic fragment are elevated in the CSF of prodromal AD patients (i.e. MCI that progresses to AD). Thus, incorporating Aβ34 as a marker of amyloid clearance with a marker of amyloid deposition (i.e. Aβ42) might complement current CSF measures, especially in clinical intervention trials that aim at a modulation of APP processing (FIG. 16). Ultimately, it is proposed that enzymatic processes affecting Aβ metabolism are altered in early phases of AD and, accordingly, Aβ34 can be used to monitor Aβ turnover at earlier stages of this devastating disease.

It is thus provided a more complete biomarker panel to assess AD samples (i.e. early-stage biochemical changes vs. late-stage plaque/tangle pathology, respectively) by combining markers of amyloid clearance (Aβ34 measurements) and deposition (well-established tau and Aβ40/42 measurements in CSF).

It is further provided treating a patient with the peptide encompassed herein which has been diagnosed for early Alzheimer's disease by detecting the level of Aβ34 in the sample by contacting the sample with an anti-Aβ34 antibody and detecting binding between Aβ34 and the antibody; wherein the level of Aβ34 in the sample is indicative that the patient has or will develop Alzheimer's disease.

As encompassed herein, the peptide is a synthetic 8-amino acid Abeta42-oligomer Interacting Peptide (AIP).

Synthetic AIP (L- or D-amino acids, RGTFEGKF-SEQ ID NO: 6), 940.5 Da) and scrambled AIP (D-amino acids, EFRKFTGG-SEQ ID NO: 7, 940.5 Da).

A unique 8-amino acid Abeta42-oligomer Interacting Peptide has been synthesized using protease-resistant D-amino acids (D-AIP) as a novel anti-amyloid strategy against Alzheimer disease (AD) pathology. Overall, the D-AIP is an orally administrable drug candidate targeting amyloid pathology based upon the unique ability of D-AIP to "trap" and neutralize toxic Abeta42 oligomers in vivo.

D-AIP peptide consist of D-amino acids of RGTFEGKF (SEQ ID NO: 6).

D-AIP is stable in mouse plasma, blood and liver S-9 fractions and ascertained the metabolic resistance towards proteases and enzymatic activities in these matrices. Overall, D-AIP appeared to be very stable in plasma and blood matrices most likely due to the resistance of this D-peptide against proteolysis. As requested for orally administrable therapeutics, the long-term (24 h) exposure of D-AIP to blood and liver enzymes mimicked a near in-vivo condition, since esterases, oxidases and peptidases are quite abundant and operative in biological matrices outside the liver, especially the blood or plasma. The signal intensity of D-AIP decreased after 24 h in the liver S-9 fractions. Likely, it is due to the enzymatic degradation by the D-amino acid oxidase (D-AAO, EC 1.4.3.3) which catalyzes the in oxidative deamination in the liver with the end products α-keto acids and ammonia. While the biostable D-AIP is not toxic, the degradation in liver is a normal physiological function to detoxify the body of foreign substances which is highly desired to avoid a long-term accumulation of D-AIP in the body.

D-AIP described herein showed favorable PK properties and penetration into the BBB in dose ranging and preclinical pharmacokinetic study with normal female and male mice after oral dosing of D-AIP. Single oral doses of 10, 30 and 100 mg/kg of D-AIP respectively were well-tolerated with no detectable vital signs of abnormalities before and after animal sacrifices. The calculated AUC values, which measured the total systemic exposure of D-AIP across the different doses throughout the duration of the study were linear in both sexes.

The obtained maximum values of concentrations in plasma, ($C_{max}$) displayed a linear relationship in both sexes indicated by respective increases in $C_{max}$ values measured. Since the $T_{max}$ in all cases were either 0.5 or 2 h, this suggests that D-AIP was rapidly absorbed in the intestine and transported to the blood stream and distribution to solid tissues. The corresponding $C_{max}$ values in both sexes across the doses are in agreement with the measured volume of distribution ($V_d$). These relatively high values of the $V_d$ across the three respective doses administered to both female and male mice showed the propensity of D-AIP to leave the plasma and enter the extravascular compartments of the body. These extravascular compartments encompass many sub-compartments such as the cellular, interstitial and lymphatic sub-compartments and a specialized system containing cerebrospinal fluid in the central nervous system. The $V_d$ values of D-AIP suggest penetration of D-AIP into brain by passive diffusion, i.e. movement across cell membranes without the input of energy. Also, the $V_d$ values suggest that D-AIP might have a relatively low protein binding property which allowed to leave the protein-rich plasma and distribution into tissues, consequently reducing the plasma half-life of D-AIP as the dose was increased. The relatively low molecular weight of D-AIP may have further facilitated the passage through the endothelia gap junctions of the capillaries into interstitial fluids in the body. Also, a label-free technique was used, MALDI-MSI, D-AIP in brain tissue which provided complementary evidence by revealing the presence of D-AIP in the specific areas of brain sections. Together, it is provided a mechanism of D-AIP entry into the brain by passive diffusion and as the intact parent molecule in the absence of any labeling.

D-AIP inhibited aggregation of Aβ42 and prevented its secondary nucleation. ThT results showed that the aggregation of Aβ42 was inhibited by D-AIP at all the ratios applied, i.e. D-AIP targeted low-order oligomers and prevented them from forming larger aggregates. Consistent with our previous findings, D-AIP at a 1:4 (D-AIP:Aβ42) molar ratio, resulted in the greatest reduction in Aβ42 aggregation, supporting preferential interaction between one D-AIP with an Aβ42 tetramer further supporting the previously postulated specificity of D-AIP binding to tetramers and low order oligomers in general. Complementary TEM images also revealed the prevention of Aβ42 aggregation by D-AIP into fibrils. Together, these two techniques (ThT and TEM) support a mechanism where D-AIP specifically targets oligomers before larger aggregates are formed by blocking the inter- and intramolecular forces required for the formation of proto-fibrils. D-AIP prevented the secondary nucleation of Aβ42, described as the formation of new nuclei catalyzed by existing fibrils, in all at a 10-fold molar excess of Aβ42 (1:10, D-AIP:Aβ42) in the ThT assay implying that D-AIP can also target higher oligomers like hexamers, octamers or 10-mers occurring in freshly prepared Aβ42 containing solutions. Thereby, D-AIP is likely affecting secondary nucleation of Aβ42, which seems to be very effective and could happen through a favourable penetration of the glycine (Gly) groove of Aβ42 oligomers by D-AIP resulting in a prevention of the secondary nucleation. As a result, D-AIP could trap and neutralize accessible neurotoxic oligomers and protofibrils. Overall, the formation of oligomers and fibrils is a step-wise process involving a rare nucleation event where a susceptible monomeric Aβ forms stable aggregates. The Aβ deposition phase, which is generally defined as one without clinical symptoms, may follow a much earlier pathogenic seed formation and propagation that presently escapes detection. Therefore, it is advantageous that D-AIP seemingly has a destabilizing effect on seeds either by inhibiting further aggregation or disaggregating them and thus arresting the further growth process of fibrils.

The D-AIP provided herewith is a novel intervention strategy. The appropriate penetration of D-AIP through the BBB into distinct brain regions is important to target early AD pathology and classifies D-AIP as a potential candidate for prevention. Its ability to prevent secondary nucleation events of Aβ42 and interruption of further fibril growth, makes it appear as a very suitable therapeutic candidate.

Example I

Synthetic Aβ-Peptides

Synthetic peptides Aβ34, Aβ35, Aβ38, Aβ40, and Aβ42 (PSL, Germany) dissolved in formic acid and vacuum-dried in a speed-vac (Thermo) were resuspended (2 mg/mL) in 1% Milli-Q/ammonia water, ultrasonicated (10 min. 4° C.), diluted to 1 mg/mL with Milli-Q and ultrasonicated again. Peptide concentrations (8=1490 $M^{-1}$ $cm^{-1}$), integrity, and molecular weight were confirmed by absorption measurements at 280 nm (Synergy H1, BioTek Instruments Inc. plate reader), Coomassie dye stains after performing denaturing polyacrylamide gel electrophoresis (SDS-PAGE), and matrix-assisted laser desorption ionization mass spectrometry (Bruker UltrafleXtreme MALDI-TOF/TOF system in standard reflector positive mode; samples mixed 1:1 with α-cyanocinnamic acid matrix and applied to ground steel targets using dried-droplet method).

BACE1-Mediated Aβ Degradation In Vitro

BACE1 from Fc purification (Bridges et al., 2006, *Peptides* 27:1877-1885) 10 pg/mL (a kind gift from Johan Lundkvist, AstraZeneca) was incubated with synthetic Aβ35, Aβ40, or Aβ42 at 50 pg/mL for 10 min. at 37° C. in 20 mM (sodium acetate/HCl, pH4.5), directly mixed 1:1 with α-cyanocinnamic acid matrix, and applied to ground steel targets using dried-droplet method.

Anti-Aβ34 Antibody

For the detection of Aβ34, a C-terminal specific antibody was generated by immunizing Balb/cJ mice with synthetic Aβ27-34 peptide (from PSL, Germany) conjugated to KLH (Thermo Scientific). Splenocytes were fused to P3×63Ag8.653 myeloma cells (ATCC). Hybridoma cultivation and antibody purification was performed as previously described (Ida et al., 1996, *The Journal of biological chemistry*, 271:22908-22914).

Surface Plasmon Resonance (SPR)

Using a BIACORE T200 system (GE Healthcare Bio-Sciences Aβ, Upsala, Sweden; v2.0 Control and v1.0 Evaluation software), SPR experiments were performed at 25° C.

using filtered (0.2 µm) and degassed HBS-EP+ buffer (10 mM HEPES PH 7.4; 150 mM NaCl; 3 mM EDTA; 0.05% (v/v) Tween™-20). Using Biacore's Amine Coupling Kit, Mouse Antibody Capture Kit, and CM5 sensors, an anti-mouse Fc antibody (14 µg/mL in 10 mM sodium acetate pH 5.0) was immobilized to the flow cells (~8000 RU each) as recommended by GE. To assess binding specificity, a variety of Aβ peptides (0-2 µM; 4-fold dilution series) were titrated over reference (anti-mouse Fc antibody only) and active (~1000 RU mab34 captured to anti-mouse Fc antibody) surfaces in single-cycle kinetic mode (25 uL/min.×5 min. association+10 min. dissociation). Between each sample series, surfaces were regenerated at 50 uL/min. using two 30 sec pulses of Pierce Gentle Ag/Ab Elution Buffer pH 6.6 (Thermo Scientific #21027) as well as 10 mM glycine pH 1.7. To assess binding affinity, Aβ34 peptide titrations (0-1.6 UM; 3-fold dilution series) were performed in the similar manner using multi-cycle kinetic mode (25 uL/min.×10 min. association+20 min. dissociation). All of the double-referenced data presented are representative of duplicate injections acquired from at least three independent trials. To predict an apparent equilibrium dissociation constant ($K_D$) for mab34, steady-state binding responses ($R_{eq}$) in the multi-cycle titrations were averaged near the end of each association phase, plotted as a function of "analyte" concentration (C), and then subjected to non-linear regression analysis ("Steady state affinity" model in Biacore evaluation software).

MSD Assay

Using the ELISA Conversion Kit from Meso Scale Discovery (MSD, USA), an electrochemiluminescence-based assay was developed (neo-epitope specific Aβ34 and the sulfo-tagged 6E10 (binds to the N-terminus of human Aβ) or the sulfo-tagged 4G8 for murine samples (binds to the mid domain of Aβ)). High-bind or custom-printed 4-plex plates (using the mab34, 4G8 (Biolegend) for pan-Aβ assay, G2-10 for 1-plex Aβ40 assay, and MSD's validated mouse monoclonal anti-Aβ38, anti-Aβ40, as well as anti-Aβ42 antibodies, see MSD Aβ peptide V-PLEX) were blocked (MSD 5% Blocker A in PBS) for 1 h at 22° C. and washed three times with PBS-T for 1 min. at 22° C., loaded with SULFO-TAG™ 6E10 or 4G8 detection antibody (diluted to 1× in MSD Diluent 100) and sample or peptide calibrator (in MSD Diluent 35 or cell culture medium), and incubated for 16 h at 4° C. with shaking at 600 rpm. After three washing steps with PBS-T for 1 min. at 22° C., 150 µL 2×MSD read buffer were added per well. All plates were read using a MSD QuickPlex SQ 120 Imager and data analyzed using MSD Workbench® software. Standard curves were fitted using a non-linear four-parameter logistic fit with $1/y^2$ weighting. The equation is:

$$y = b_2 + \frac{b_1 - b_2}{1 + \left(\frac{x}{b_3}\right)^{b_4}}$$

y=signal, x=concentration, $b_2$=estimated response at infinite concentration, $b_1$=estimated response at Zero concentration, $b_3$=mid-range concentration, $b_4$=slope factor.

In the WORKBENCH® software, lower limit of detection LLOD was determined as the analyte concentration equivalent to the signal that is 2.5× standard deviation (SD) above the back-fit signal of the blank. Assay performance (inter-plate, intra-plate CV, LLOD, and upper limit of detection (ULOD)) were assessed using peptide calibrators in MSD diluent 35 (FIG. 2e). Spike-and-recovery and linearity-of-dilution assessments for human CSF samples (compared with calibrators in MSD diluent 35) are given in Table 1.

TABLE 1

| Spike-and-recovery and linearity-of-dilution assessments for CSF-Aβ34 with MSD | | |
|---|---|---|
| | n | mean Recovery [%] (SD) |
| neat | 4 | 100 |
| 1:2 | 4 | 115 (2) |
| 1:4 | 4 | 114 (1) |
| 1:8 | 4 | 105 (2) |
| Spike low (1 ng/mL) | 4 | 81 (3) |
| Spike high (3 ng/mL) | 4 | 85 (3) |

Western Blot Analysis

LDS loading buffer (Invitrogen) with 2-Mercaptoethanol (final concentration 5% (v/v)) was added to samples and the mix was heated to 70° C. for 10 min. Proteins were separated on 4-12% bis/tris gradient gels. Novex® Sharp Pre-Stained Protein Standard (Invitrogen) was used. Peptides/proteins were transferred onto polyvinylidene fluoride (PVDF) membranes (Millipore) by tank blotting (Biorad) at 4° C. The primary antibodies, anti-actin C4 (Millipore), anti-APP ectodomain 22C11 (Millipore), anti-BACE1 D10E5 (Cell Signaling), anti-sAPPβ (IBL), and secondary antibodies (Horseradish Peroxidase-Conjugated anti-mouse, anti-rabbit, Promega), were used according to the manufacturer's instructions. Signals were recorded on ImageQuant LAS 500 or Amersham Imager 600 (GE Healthcare Life Sciences).

Mouse Brain Lysates

Brains were obtained from BACE1−/− and BACE1+/− mice, as well as their wild type littermates (Dominguez et al., 2005, The Journal of biological chemistry, 280:30797-30806) in accordance with the guidelines of the Institutional Animal Care and Use Committee at the University of Kiel. Frozen mouse brains were thawed on ice, weighed and homogenized in 100 mM Tris-HCl, 150 mM NaCl, 2× complete protease inhibitor cocktail (Roche) using gentleMACS™ M Tubes/Dissociator at 4° C. (Miltenyi Biotech). TritonX-100 was added for a final concentration of 1% and brain homogenates were lysed for 1 h at 4° C. Lysates were centrifuged at 10,621 rcf in a microfuge (Eppendorf) at 4° C. for 15 min. to remove nuclear fraction. Samples were diluted in the appropriate buffers for protein determination using bicinchoninic acid assay (BCA assay, Pierce) and MSD assays.

Pharmacological Treatment of Rats

Experiments were approved by the McGill Animal Care Ethics Committee. 6-8 weeks old male Sprague Dawley rats were housed at the Douglas Mental Health University Institute animal facility and treatments were performed in accordance with the guidelines of the Canadian Council on Animal Care. Rats were intravenously injected with indicated concentrations of MK-8931 (Selleckchem) or vehicle (20% Cyclodextrin) and samples were collected after 1 h of treatment. CSF was collected with the aid of a stereotaxic instrument to appropriately position the head of the rat and samples stored at −80° C. Brain tissue samples were harvested and immediately preserved on dry ice, later stored at −80° C. Brain lysates were prepared as described above (see mouse brain lysates).

Plasmids-Mutagenesis

Human full length BACE1 (isoform A) and human full length APP (isoform APP695, with an N-terminal Myc tag and a C-terminal FLAG tag), in the mammalian expression vector pCEP4, Hygro (Invitrogen) were used for expression. All constructs were verified by DNA sequencing.

Cell Culture and Transfection

Human neuroblastoma (SH-SY5Y) cells (DSMZ No.: ACC 209; DSMZ, Braunschweig/Germany) were cultured in 50% DMEM, 50% Hams-F12, 10% fetal bovine serum (FBS), 2 mM L glutamine, 0.5 mM sodium pyruvate, 1×MEM non-essential amino acid solution in a humidified incubator at 37° C. with 5% CO2. Cells were routinely tested for *mycoplasma* contamination. SH-SY5Y cells were transfected using TransFectin™ according to the manufacturer's instructions (BIORAD) and stable clones were selected using 250 µg/ml Hygromycin B. For experiments, culturing medium without Hygromycin B was used and conditioned for 16 h. Protease inhibitors, were dissolved in DMSO at a 1000× concentration and compared to vehicle treatment (DMSO 1:1000). Cells were harvested on ice. Cell culture supernatants were collected, centrifuged for 10 min. at 450 rcf in a microcentrifuge at 4° C. and used for further analysis. Cells were washed once on ice with ice-cold PBS$^{++}$ and lysed in 20 mM Tris-HCl, pH 7.5, 150 mM NaCl, 20 mM 3-[(3-cholamidopropyl)dimethyl-ammonio]-1-propanesulfonate (CHAPS), 2× Complete protease inhibitor (Roche), for 60 min. at 4° C. Cell lysates were centrifuged for 15 min. at 10,621 rcf in a microcentrifuge at 4° C. to remove nuclear fraction.

CSF Samples

CSF samples for initial assay development were received from the Clinic at the Division of Psychiatry, Zurich. CSF samples from individuals with SILK data (Patterson et al., 2015, *Ann Neurol*, 78:439-453) were obtained from the Department of Neurology, Washington University in St. Louis. CSF samples from individuals with different clinical diagnoses were received from the Amsterdam Dementia Cohort and the time interval between CSF collection and assessment of cognition was less than 24 h (van der Flier et al., 2014, *Journal of Alzheimer's disease: JAD*, 41:313-327). CSF samples from cognitively normal individuals at risk for Alzheimer's disease (PREVENT-AD study) were received from the Douglas Mental Health University Institute and the time interval between CSF collection and assessment of cognition was on average 5.6±3.9 (SD) months (Breitner et al., 2016, The Journal of Prevention of Alzheimer's Disease (JPAD), 3 (4): 236-242). The experimentalist was blinded from diagnosis until completion of measurements. Diagnoses of probable Alzheimer's disease (McKhann et al., 1984, *Neurology*, 34:939-944) or MCI (Petersen et al., 1999, *Arch Neurol*, 56:303-308), were made by consensus of a multidisciplinary team according to diagnostic criteria. For the Amsterdam Dementia Cohort, patients who presented with cognitive complaints but were considered as normal after thorough investigation (i.e. criteria for MCI, dementia or any psychiatric or neurological results not fulfilled) were defined as patients with subjective cognitive complaints (SC). Subjects were followed annually and MCI to AD conversion (or MCI that remained stable) was defined based on conversion to AD within 3 years after the CSF collection, and stable as no conversion occurred within 3 years. Lumbar punctures (LPs) after an overnight fast were performed using the Sprotte 24-gauge atraumatic needle. Samples were aliquoted into propylene cryotubes and stored at −80° C. Procedures from the BIOMARK-APD consortium of the EU Joint Program in Neurodegenerative Disease were used for sample preparation and measurements (Del Campo et al., 2015, *Front Neurol*, 6:202). A summary of samples included in the study is given in Table 2. CSF t-tau, p-tau, and Aβ42 were measured using INNOTEST ELISA; Fujirebio (formerly Innogenetics).

TABLE 2

Number and age of Individuals in the Separate Studies

| | cognitively normal | SC | MCI | AD |
|---|---|---|---|---|
| Amsterdam Dementia Cohort (n = 98) | | n = 22 | n = 44 | n = 32 |
| female | | 13/22 | 19/44 | 17/32 |
| ε4-carrier (%) | | 45 (two missing values) | 63 (one missing value) | 71 (one missing value) |
| Cognition, Mini-Mental State Examination score (SD) | | 27.7 (1.4) | 26.5 (2.1) | 23.3 (4.9) |
| Age in years (SD) | | 59.5 (8.1) | 67 (8.1) | 65.3 (7.7) |
| PREVENT-AD (n = 94) | n = 94 | | | |
| female | 64/94 | | | |
| ε4-carrier (%) | 37 | | | |
| Cognition, Montreal Cognitive Assessment score (SD) | 27.8 (1.6) | | | |
| Age in years (SD) | 63.1 (5.8) | | | |

Statistical Analysis

The statistical evaluation was carried out by GraphPad Prism, SPSS, MedCalc Version 18.2.1, and the indicated statistical tests and algorithms (ANOVA, t-test, Pearson correlation, Mann Whitney U tests, Spearman correlations, De Long statistics to compare ROC curves) (DeLong et al., 1988, *Biometrics*, 44:837-845). The optimal cut-off (point on the ROC curve with the minimum distance (d) to sensitivity=1 and specificity=1) was determined using Pythagoras' theorem:

$$d = \sqrt{(1 - \text{sensitivity})^2 + (1 - \text{specificity})^2}$$

Individual data points, mean and s.e.m are displayed. Data were tested for normality, using violation of the Shapiro-Wilk test at p<0.01 as the criterion. Data sets not meeting the normality assumption were analyzed using non-parametric tests.

Example II

D-AIP Characterization

Synthetic AIP (L- or D-amino acids, RGTFEGKF, 940.5 Da) and scrambled AIP (D-amino acids, EFRKFTGG, 940.5 Da) were produced by BioBasic (Markham, ON, Canada) and were verified by mass spectrometry. Freshly prepared AIP peptides were solubilized at 1 mg/ml in deionized water, vortexed and then sonicated at 37 Hz and 100% power for 10 min at 4° C. Synthetic Aβ42 peptides were purchased from Bachem peptides, Germany. Aβ42 peptide was monomerized and solubilized as described (Barucker et al., 2015, Sci Rep, 5:15410). Briefly, monomerized peptides were dissolved to 1 mg/ml in deionized water supplemented with ammonia to a final concentration of 0.13% (measured pH 9.8). Resuspended AIP and Aβ42 peptide were diluted to 0.5 mg/ml respectively in TA50 (acetonitrile: 0.1% (v/v) trifluoracetic acid TFA=50:50) to verify its intact mass by MALDI-MS (Bruker Ultraflextreme system) and its sequence verification by ESI-MS (Bruker Impact II system).

The stability of D-AIP in mouse plasma, blood and liver S-9 fraction was investigated to ascertain the metabolic resistance towards proteases and enzymatic activities in these matrices. Whole mouse blood obtained from healthy C57BL/6 male and female mice (6 mice in total) were collected in lithium heparin containing tubes, pooled and stored at 4° C. prior to its use. A fraction of the pooled blood was immediately centrifuged at 1500×g for 10 min at 4° C. to obtain the plasma. The whole blood and plasma samples were spiked with PBS (as control) or AIP (L-AIP, D-AIP or sD-AIP respectively) to make a final concentration of 1 ug/mL and incubated at 37° C. Initial samples were withdrawn to represent t=0 prior to incubation and others were withdrawn 1, 3 and 24 h respectively. Fresh mouse liver also obtained from C57BL/6 male and female mice were pooled, homogenized in 0.15 M Potassium chloride (KCl) and centrifuged at 9000×g. The supernatant represents liver homogenate (S-9) fraction which was mixed with other buffers to formulate the liver S-9 mix as previously described (Kolrep et al., 2017, Toxicol In Vitro, 42:161-170). Liver S-9 mix were spiked with AIP to make a final concentration of 1 µg/mL (L-AIP, D-AIP or sD-AIP respectively) and incubated at 37° C. Just after the addition of NADPH, 100 µL aliquot which represents t=0 samples were withdrawn and others were sampled accordingly at predetermined time points. 400 µL of ice cold MeOH was added to the spiked plasma, blood or liver S-9 fraction respectively, to precipitate the microsomal protein. The samples were then vigorously mixed for 30 s to facilitate extraction and centrifuged for 10 minutes at 13000 rpm, the supernatant was subjected to sample clean up by $C_{18}$ ZipTip (EMD Millipore Corporation), the eluates were spotted with CHCA matrix on the ground steel MALDI-TOF target and analyzed with MALDI-TOF MS. Applying the t=0 peak area as 100% the intensities of the other time points were compared relatively for interpretation. ZipTip is a 10 µL pipette tip with a bed of chromatography media fixed at its end with no dead volume, and thus it's an ideal tool for concentrating and purifying samples for sensitive analyses.

An internal standard (IS) for the reliable quantification of D-AIP in biological matrices was prepared by dimethylation to produce an analog of D-AIP by using a protocol previously described (Boersema et al., 2009, Nat Protoc, 4:484-494). Standard solutions (1 mg/mL) each of D-AIP and IS were prepared in deionized water and 100% methanol respectively. 100 µL of IS working solution was prepared at 50 ng/ml added to 25 µL of the sample (plasma or brain homogenate). The sample was vortexed for approximately 5 s and let stand for 10 min, then centrifuged at 16,000 g for 10 min. The supernatant was transferred to a 13×100 polypropylene tube and evaporated to dryness at 50° C. under gentle stream of nitrogen. The dry extract was re-suspended with 40 µL of 0.1% (v/v) formic acid (Sigma Aldrich, St-Louis, MO, USA) in deionized water and transferred to an injection vial for analysis.

Thermo Scientific TSQ Quantiva Triple Quadrupole mass spectrometer (San Jose, CA, USA) was interfaced with the Thermo Scientific UltiMate 3000 XRS UHPLC system (San Jose, CA, USA) using a pneumatic assisted heated electrospray ion source. Data acquisition and analysis were performed using Xcalibur 4.0 (San Jose, CA, USA).

☐radient elution was used with a Thermo Scientific BioBasic-8 column (100×2 mm I.D. 5 µm) operating at 40° C. The initial mobile phase condition consisted of 0.1% formic acid in acetonitrile and 0.1% formic acid in deionized water at a ratio of 5:95, respectively and this ration was maintained for 1 min. A linear gradient was applied from 1 to 5 min up to a ratio of 50:50 and maintained for 1 min. At 6.1 min, the mobile phase composition was reverted to 5:95 and the column was allowed to equilibrate for 7.9 min for a total run time of 14 min. The D-AIP and IS eluted at 4.7 and 4.8 min respectively at a fixed flow rate of 0.2 mL/min. The eluent was diverted to waste for the first minute and last six minutes. Extracted sample (5 µL) was injected and the acquisition time was set to 14 min.

The mass spectrometer was interfaced with ultra-high-performance liquid chromatography (UHPLC) system using a pneumatic assisted heated electrospray ion source with detection in positive ion mode using multiple ion monitoring (MRM). For proper optimization of the mass spectrometer, standard solutions of D-AIP and IS were infused. The obtained source parameters were 50 and 15 arbitrary units respectively while using nitrogen for the sheath and auxiliary gases. The HESI electrode was set to 3500 V, capillary and vaporizer temperature were both set to 300° C. respectively. The MS/MS parameters were optimized using the doubly charged species. Argon was used as collision gas at a pressure of 2.5 mTorr. The precursor-ion reaction for D-AIP were set to 471.4→[591.8+648.3] and for the IS the MRM transitions were set to 499.4→[425.8+468.8+476.8]

Standard solution of D-AIP (1 mg/mL) was diluted in various volumes of deionized water to obtain series of standard working solutions. Calibration standards were prepared by fortifying the mouse plasma and mouse brain homogenate with the standard working solutions at 10% (v/v) to enable analytical concentration range of 1.00 to 1000 ng/ml. The method is linear using a linear regression weighted 1/x analysis, a value of $R^2 \geq 0.9979$ was obtained for plasma and $R^2 \geq 0.9991$ for brain homogenate. Samples were injected in duplicate with the calculated in each case and concentrations were processed from the equation obtained from the respective calibration curves using Xcalibur 4.0 software.

Animal care and all animal experiments were undertaken with federal guidelines and approval of the Institutional Animal Ethical Committee of McGill University, Montreal, Canada (Protocol Application Number: 2017-7880) and adequate measures were taken to minimize pain or discomfort. C57BL/6 mice were purchased from Charles River laboratories, a total of 144 healthy (7-9 weeks old) male and female (20-25 g) were grouped accordingly and housed in polycarbonate cages, (three mice per cage per sex) in air-conditioned rooms with a 12 h light/dark cycle. Animals were allowed unlimited access to drinking water and standard mouse chow during the study. Animals (n=3) were orally dosed with D-AIP using an oral gavage at 10, 30 and 100 mg/kg respectively prepared in phosphate buffered saline (PBS). Animals were euthanized with 5% isoflurane followed by cervical dislocation. Blood collection (approximately 500 µL each) in lithium heparin containing tubes (BD microtainer, NJ, U.S.A) were by intracardiac puncture at 0.5, 2, 4, 6, 8, 12, 24 h post-dose. Control animals were orally dosed with PBS and euthanized as described above at 3 h post administration. All blood samples were centrifuged at 1500×g for 10 min at 4° C. and aliquots of plasma (approximately 0.5 mL) were immediately kept on dry ice and later stored at −80° C. prior to analysis. Brains were surgically removed from all animals and immediately frozen on dry ice prior to storage at −80° C. Pharmacokinetic parameters area under the curve (AUC), maximum concentration reached ($C_{max}$), time at which maximum concentration is reached ($T_{max}$). elimination rate constant (A), elimination half-life ($t_{1/2}$), apparent total clearance from plasma after oral administration (CI/F), apparent volume of distribution ($V_d$) and mean residence time (MRT) were calculated using PKSolver, a freely available menu-driven add-in program for Microsoft Excel written in Visual Basic for Applications (VBA), for solving problems in pharmacokinetics.

For the MALDI imaging study, additional four mice (two males and two females) were orally dosed either with PBS or D-AIP (10 mg/kg) and sacrificed 4 h post-administration (at the time maximum concentration was reached in the lowest dose) as described above. Frozen brains were stored at −80° C. until needed for analysis. Serial sagittal brain sections (10 μm thick) obtained using a cryostat (Leica Microsystems CM1100, Wetzlar, Germany), were thaw mounted onto an indium tin oxide (ITO) coated glass slide (Bruker, Bremen, Germany). Glass slides were removed from deep freeze and immediately transferred to a vacuum desiccator. Following 12 h desiccation time, the slides were scanned using a flatbed scanner (HP LaserJet 3055). The α-cyano-4-hydroxy cinnamic acid (CHCA) matrix (10 mg/mL) was prepared in 50% acetonitrile (ACN) containing 0.1% trifluoroacetic acid (TFA). The matrix solution was sonicated for 10 min and centrifuged at 10 000 rpm for 10 min before transfer to the ImagePrep (Bruker Daltonics). An automatic spraying device that deposits matrix solution onto the tissue in a consistent manner under controlled conditions as previously described (Shobo et al., 2015, Assay Drug Dev Technol, 13:277-284). A standard solution of D-AIP (1 μg/mL was analyzed using matrix assisted laser desorption ionization time of flight mass spectrometry (MALDI TOF MS) operated both at reflectron and MALDI MS/MS (LIFT) modes respectively with the aid of the UltraflExtreme MALDI TOF/TOF 2 KHz smartbeam laser (Bruker Daltonics, Bremen, Germany) and FlexControl acquisition software ran in positive ion mode. The instrument was calibrated using standard peptide mix spotted with CHCA matrix on the ground steel target (Bruker Daltonics, Bremen, Germany) for 500-1500 m/z. Each spectrum was acquired from 500 laser shots. The LIFT experiments were performed using a method optimized for the drug by specific tuning of the timing of the LIFT cell and of the precursor ion selector. The LIFT method was calibrated with peptide calibration standards and also a standard solution of D-AIP as mentioned above. Tissue sections were imaged with spatial resolution 50 μm. The MALDI images were processed using the FlexImaging 4.0 software (Bruker Daltonics, Bremen, Germany).

Freshly monomerized synthetic Aβ42 peptide was dissolved as previously described above. The final concentration was verified by spectrophotometry, using a Synergy H1 multi-mode microplate reader (BioTek; £280=1490 M$^{-1}$ cm$^{-1}$ for Aβ42), and adjusted if required by addition of 0.5% (v/v) ammonia water. ThT solution was diluted in PBS (20 mM Na$_2$HPO$_4$, 150 mM NaCl, pH 7.4) in a threefold molar excess to the desired Aβ concentration, before Aβ42 with or without D-AIP, making up a final volume of 300 μL. Measurements were performed in triplicates, for which 100 μL of the solution were transferred per well on a black Nunc Microwell 96-Well Optical-Bottom Plate (ThermoFisher Scientific). Controls were included for each peptide concentration, containing the threefold concentration of ThT but no peptide. The plate was sealed using protective foil to avoid evaporation in the course of the measurement. Fluorescence was measured at 485 nm upon excitation at of 450 nm every 5 min for a total of 40 h, at room temperature. Control values were ultimately subtracted at each time point for normalization.

Aβ peptides were dissolved to 40 UM and incubated for 24 h at room temperature with or without D-AIP at a ratio of 1:20 (Aβ42:AIP). After 24 h incubation, a portion without D-AIP was then added with appropriate amount of D-AIP (1:20) and further incubated for another 24 h. Aliquots (4 μL) of matured peptide solutions in all instances were applied to glow-discharged carbon-coated copper grids (Electron Microscopy Sciences, EMS300-Cu) and negatively stained with 2% aqueous uranyl acetate as described (Scarff et al., 2018, J Vis Exp). Data was collected on a FEI Tecnai G2 Spirit Twin electron microscope operated at 120 kV with a Gatan Ultrascan 4000 CCD camera at the Facility for Electron Microscopy Research at McGill University. In an attempt to further characterize the structural state of the Aβ42 aggregates interacting with D-AIP, immediately after spotting on the glow-discharged carbon-coated copper grids of the TEM in both experiments (i.e. co-incubation of freshly prepared Aβ42 with D-AIP and preformed aggregates with D-AIP respectively as earlier described), the rest of the samples were centrifuged at a speed of 13,000 rpm for 10 min, and residue spotted with sDHB matrix on the polished steel MALDI-TOF target for mass acquisition using linear positive mode of the MALDI-TOF MS. Spectrums were acquired using the MALDI-TOF MS to observe the current state of the incubated Aβ42 with or without D-AIP.

Figure 17A:
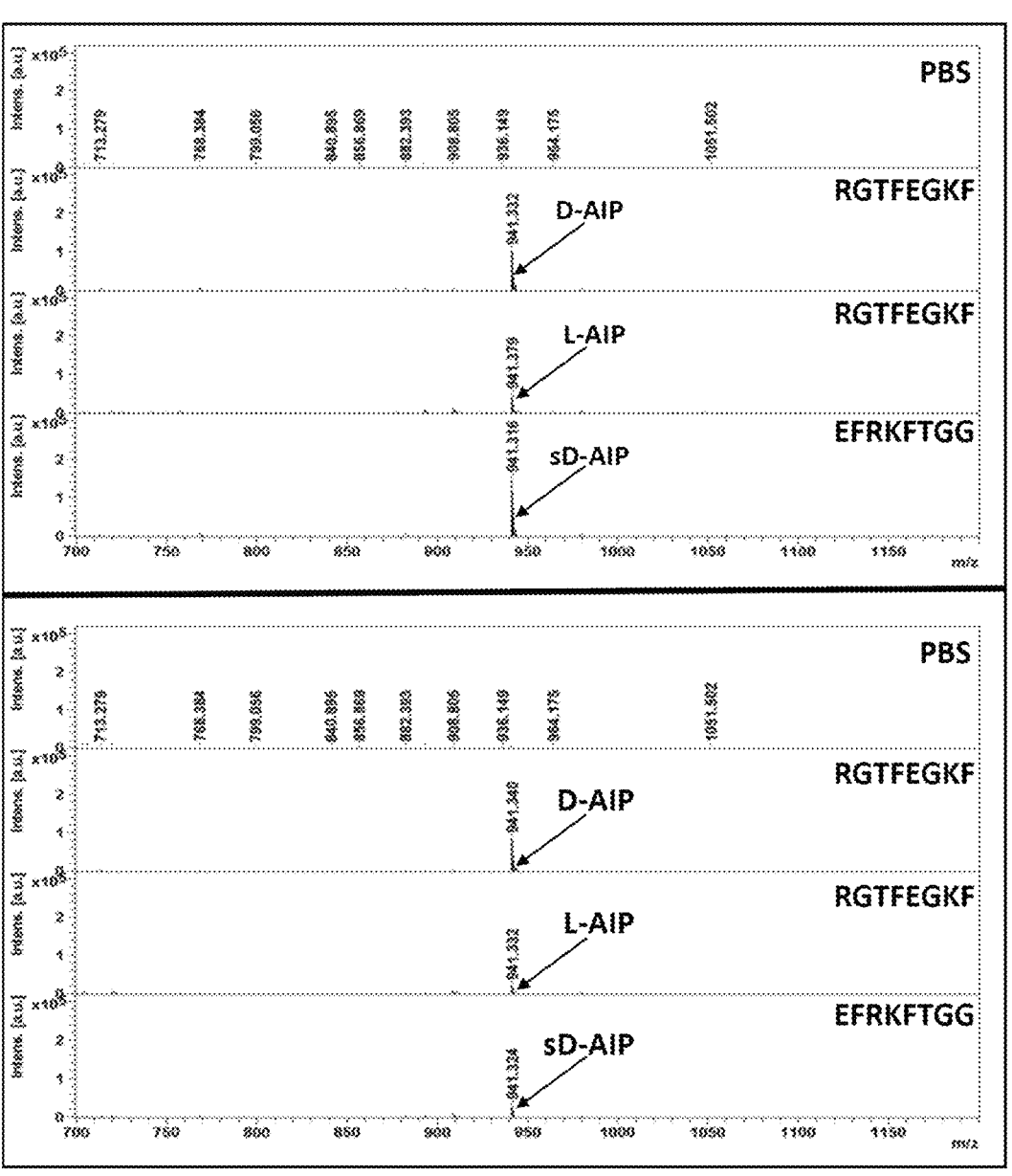
FIG. 17A illustrates the ex-vivo stability of D-AIP in mouse plasma, wherein D-AIP (RGTFEGKF), L-AIP (RGT-FEGKF), sD-AIP (EFRKFTGG) and phosphate buffered saline (PBS) as control were spiked into mouse plasma and incubated at 37° C. for 24 h (lower panel) and non-incubated spiked plasma served as control (upper panel), and MALDI-TOF MS spectra showed that D-AIP (941 m/z) was rela-tively stable over 24 h in mouse plasma whereas L-AIP (941 m/z) diminished to about a third of the initial intensity signal under the same condition.
Figure 17B:
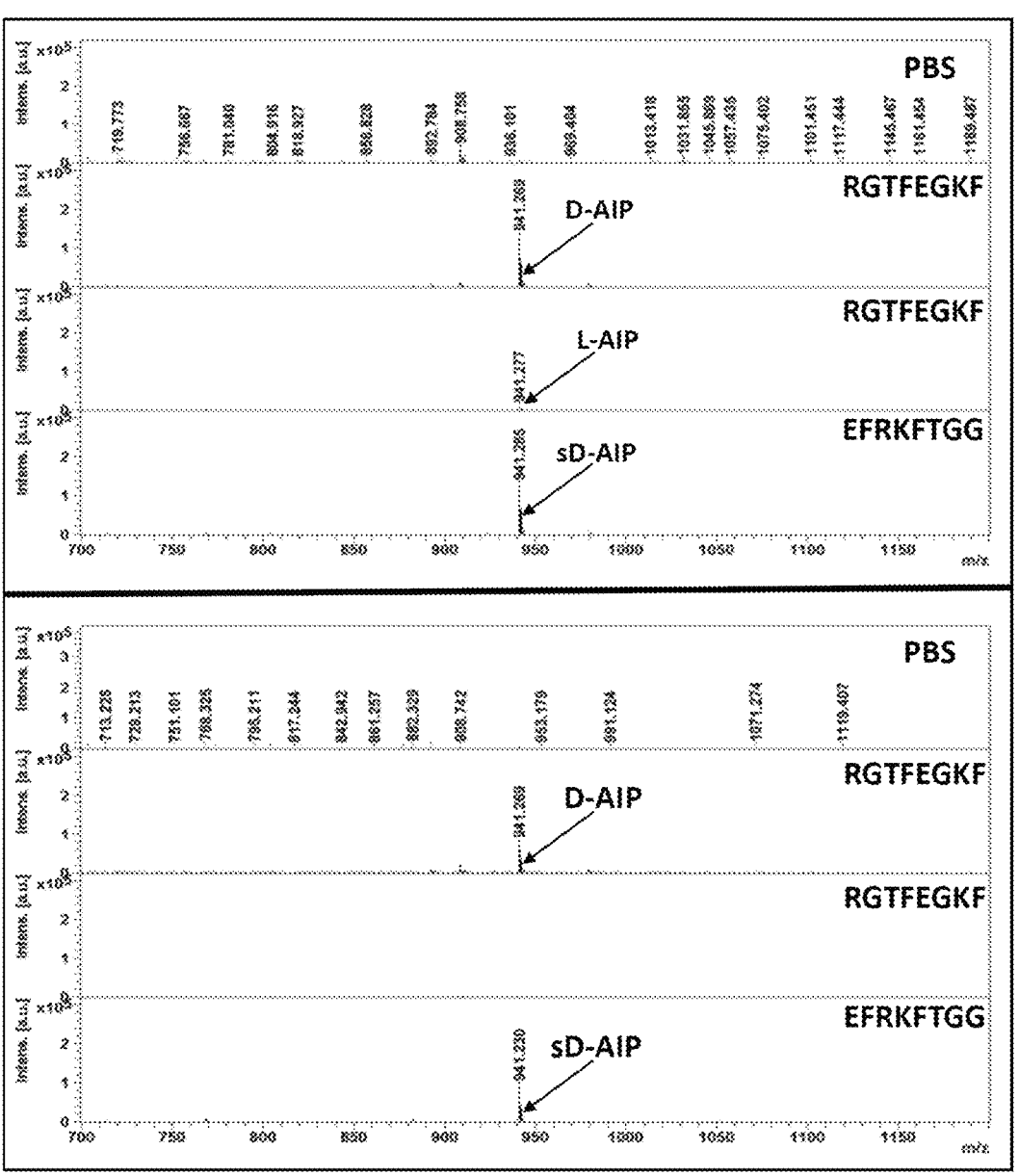
FIG. 17B illustrates the ex-vivo stability of D-AIP in mouse whole blood, wherein D-AIP (RGTFEGKF), L-AIP (RGTFEGKF), SD-AIP (EFRKFTGG) peptides were spiked into mouse whole blood and incubated for 24 h at 37° C. (lower panel) and non-incubated spiked blood served as control (upper panel), and MALDI-TOF MS spectra showed that D-AIP (941 m/z) was relatively stable up to 24 h in the mouse blood whereas L-AIP (941 m/z) was no longer detectable under the same condition.
Figure 17C:
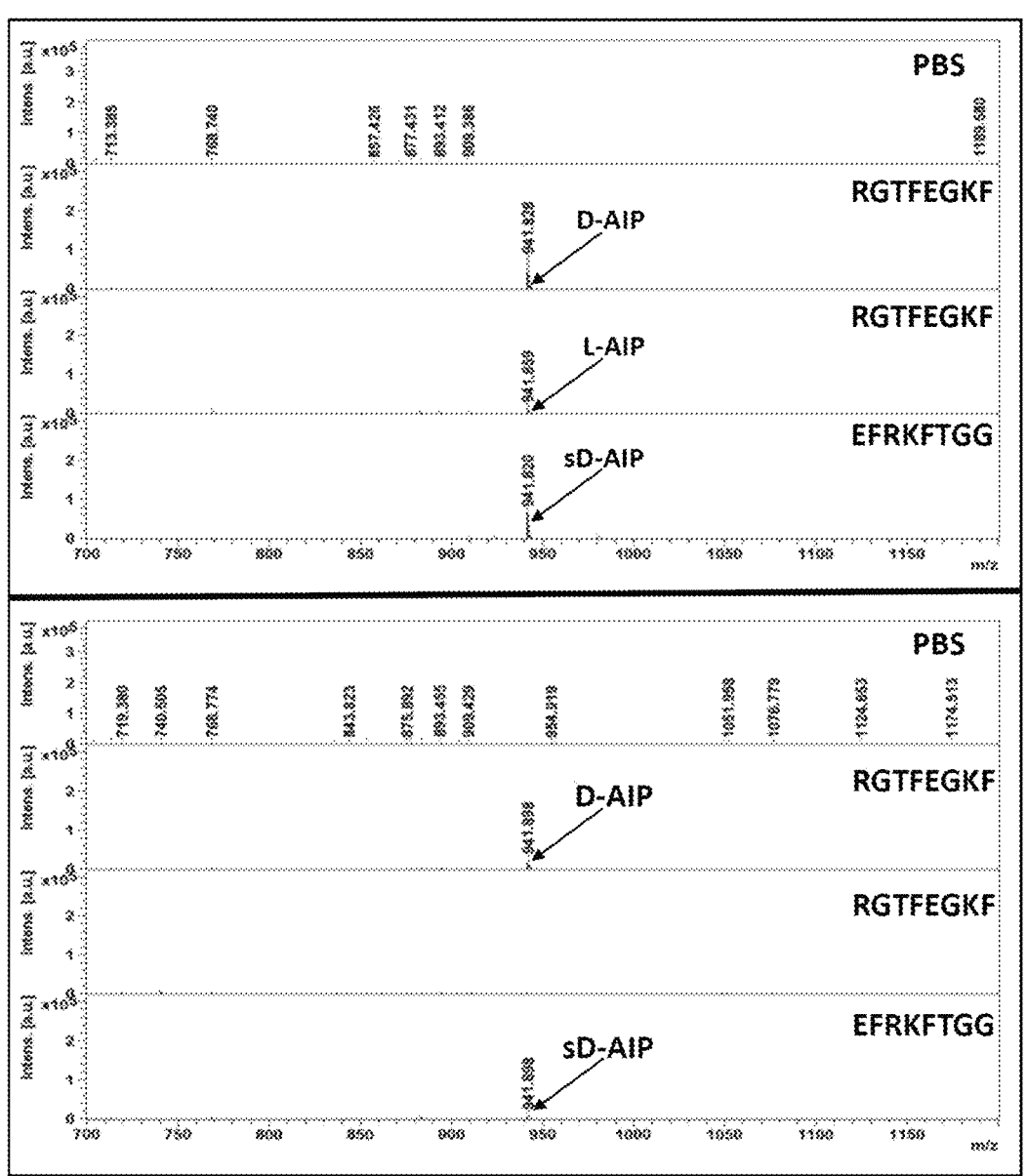
FIG. 17C illustrates the ex-vivo stability of D-AIP in mouse liver S9-fraction, wherein D-AIP (RGTFEGKF), L-AIP (RGTFEGKF), SD-AIP (EFRKFTGG) and phos-

To mimic oral administration and access the first-pass effect of the liver on D-AIP, liver S-9 fraction were incubated with D-AIP. The stability of D-AIP was evaluated in pooled samples taken from normal male and female mice after D-AIP was spiked and incubated at 37° C. for 1, 3 and 24 h in these biological matrices. The multi-time point aliquots were biochemically processed and analyzed by MALDI-time of flight (TOF) MS acquisition. A phosphate buffered saline (PBS), protease-sensitive L-AIP synthesized from L-amino acids and a scrambled version of D-AIP (sD-AIP) served as controls in this study. Peak intensities revealed a decreasing order in blood>plasma>liver of D-AIP stability which was similar for sD-AIP at all-time points (FIG. 17A-C). The stability of L-AIP was assessed in whole mouse blood at time 0 showing already a low peak intensity at the begin of incubation and the signal was below the detection limit after 24 h incubation time (FIG. 17B). A fast and early degradation of L-AIP was further indicated by lower signal intensities at 1 and 3 h time points, respectively. In contrast, signals of D-AIP and its scrambled variant (sD-AIP) decreased by approximately 50% over 24 h incubation time but remained easily detectable in the mouse whole blood even after 24 h. D-AIP in mouse liver S-9 fraction after 24 h showed a three-fold decreased intensity and sD-AIP revealed a four-fold reduced intensity in mouse liver S-9 fraction after 24 h compared to the unincubated sample, indicating relative stability. In contrast, the L-AIP signal as expected was absent after 24 h incubation in mouse liver S-9 fraction (FIG. 17C). Overall, a general trend in reduced peak intensities was observed for all three peptides after 3 h indicating biodegradability in the liver S-9 fraction. Accordingly, D-AIP appeared to be very stable in plasma and blood matrices which is expected for D-peptides and confirms the expected level of resistance against proteolysis. The long-term (24 h) exposure of D-AIP to blood and liver enzymes has proven the stability of D-AIP under in-vivo conditions which is required for orally administrable compounds in these matrices under exposure conditions chosen.

To investigate PK properties and potency of drug penetration of the BBB, a dose ranging pharmacokinetic study was performed with normal female and male mice after oral dosing of D-AIP. To quantify D-AIP in plasma obtained from female and male 7-9 weeks old C57BL/6 mice (n=3)

after a single oral dose, a sensitive and rapid biochemical LC-MS method was developed. The PK properties of D-AIP was evaluated after the administration of the respective dose of 10, 30, 100 mg/kg. A summary of the pharmacokinetic parameters obtained is given in Table 3.

TABLE 3

Pharmacokinetic Parameters of D-AIP in plasma

| | Gender | | | | | |
|---|---|---|---|---|---|---|
| Dose (mg/kg) | Female 10 | Male 10 | Female 30 | Male 30 | Female 100 | Male 100 |
| | Pharmacokinetic parameters | | | | | |
| $AUC_{0-t}$ (ng h $mL^{-1}$) | 261.11 | 270.86 | 643.10 | 825.73 | 1928.30 | 2041.98 |
| $AUC_{0-inf}$ (ng h $mL^{-1}$) | 332.92 | 279.27 | 713.88 | 823.96 | 1940.09 | 2049.79 |
| $C_{max}$ (ng $mL^{-1}$) | 48.41 | 41.52 | 76.57 | 123.53 | 372.25 | 332.51 |
| $T_{max}$ (h) | 2.00 | 2.00 | 2.00 | 0.50 | 0.50 | 0.50 |
| $\lambda_z$ ($h^{-1}$) | 0.06 | 0.15 | 0.10 | 0.21. | 0.21 | 0.24 |
| $T_{1/2}$ (h) | 11.92 | 4.56 | 6.70 | 3.23 | 3.34 | 2.91 |
| CL/F (L $h^{-1}$) | 30.04 | 35.81 | 42.02 | 36.02 | 51.54 | 48.79 |
| $V_d$/F (L) | 516.64 | 235.34 | 406.00 | 167.76 | 248.74 | 204.84 |
| MRT (h) | 14.37 | 6.42 | 9.57 | 5.85 | 4.47 | 5.29 |

* Values represent concentrations obtained from average of 3 animals (n = 3) in each case.

The $AUC_{0-t}$ values in females were 261.11, 643.10 and 1928.30 ng h $mL^{-1}$ while the males had 270.86, 825.73 and 2041.98 ng h $mL^{-1}$ following respective single oral doses of D-AIP at 10, 30 and 100 mg/kg after 24 h post-administration. These doses yielded maximum plasma drug concentrations ($C_{max}$) in females of 48.41, 76.57 and 372.25 ng $mL^{-1}$ and in males of 41.52, 123.53, and 332.51 ng $mL^{-1}$ respectively.

Maximum concentrations ($C_{max}$) were reached in female plasma after 2 h with 10 and 30 mg/kg doses and after 0.5 h for the 100 mg/kg dose. $T_{max}$ in males was reached after 2 h for the 10 mg/kg dose and 0.5 h for higher doses, i.e. 30 and 100 mg/kg. The elimination rate constant (A) in the females were 0.06, 0.10, and 0.21 $h^{-1}$ while rates were determined to be 0.15, 0.21 and 0.24 $h^{-1}$ in males at 10, 30 and 100 mg/kg respectively. The elimination half-life (tv) in the female mice measured were for 10, 30 and 100 mg/kg doses 11.92, 6.70, and 3.34 h, while 4.56, 3.23 and 2.91 h were measured for males. The apparent total clearance (CL/F) of the D-AIP from plasma after respective oral doses given to female mice were 30.04, 42.02, 51.54 L $h^{-1}$ while the corresponding values for males were 35.81, 36.02, 48.79 L $h^{-1}$. Volume of distribution ($V_d$) values were 516.64, 406.00 and 248.74 L in females after administration while it reached 235.34, 167.76 and 204.84 L in the males. The values for the mean residence time (MRT) in the female mice were 14.34, 9.57 and 4.47 h, however MRT values in males reached 6.42, 5.85 and 5.29 h after they were dosed with 10, 30 and 100 mg/kg respectively. The D-AIP concentration-time profiles in plasma (FIG. 18) show the absorption of D-AIP into the plasma in female (FIG. 18A) and male (FIG. 18B) C57BL/6 mice. D-AIP plasma concentrations in plasma declined and reached baseline levels after 24 h in both sexes and at all doses administered suggesting that D-AIP was distributed to tissues and eliminated from the peripheral system over time. The D-AIP plasma profiles of all animals treated resembled each other to a high degree with very few exceptions which are due to physiological factors including sex-related drug metabolism. Single oral doses of all concentrations of D-AIP tested were well-tolerated with no detectable vital signs of abnormalities before and after animals were sacrificed. The calculated AUC values, which measured the total systemic exposure of D-AIP across the different doses throughout the duration of the study, were linear in both sexes.

The BBB is a structural and functional semipermeable border of endothelial cells between the interstitial fluid of the brain and the blood. To evaluate the potency of D-AIP to cross the BBB, D-AIP brain concentrations were determined after respective single oral dose treatments (10, 30 and 100 mg/kg) of female and male 7-9 weeks old C57BL/6 mice (n=3). Concentrations were analyzed in brain homogenates of different time points by our sensitive LC-MS method (FIG. 19). The D-AIP brain concentrations reached maximum value with respective doses of 10, 30 and 100 mg/kg in female mice of 28.91 ng/g at 4 h, 136.29 ng/g at 2 h and 707.95 ng/g at 2 h (FIG. 19). The male mice reached peak concentrations of 133.15 ng/g, 262.00 ng/g and 509.24 ng/g after the respective doses at 4 h, 2 h and 0.5 h.

These data confirmed that D-AIP peptides enter and exit the CNS of mice of both sexes, likely by so far uncharacterized transport systems with the participation of capillary endothelial cells of the neurovascular unit. At the highest dose administered, the D-AIP brain profile showed most rapid (within 0.5-2 h) transport to the brain in male mice with gradual elimination from the brain reaching a concentration of 38.55 ng/g after 4 h. Surprisingly, D-AIP levels rapidly decreased to 16.67 ng/g in female animals indicating a more efficient elimination of D-AIP from the female brain within 2 h which is in contrast to 4 h in male mice (FIG. 19). This might have been caused by the possible differences in body physiology as also noticed in plasma concentration profiles.

Two female and two male C57BL/6 mice after administering a single oral dose either with PBS or D-AIP (10 mg/kg), sacrificed animals after 4 h and applied the appropriate mass filter (D-AIP=941 m/z) to generate a 'heat map' indicating the relative intensity (low: blue) to high (white) and position of D-AIP within sagittal brain sections at 50 μm resolution. The D-AIP distribution in representative sagittal brain sections of dosed female and male revealed intense, green to pink-colored heat maps essentially along the cortex to the hippocampus and thalamus structures (FIG. 420). In comparison to the male animals analyzed, female brain sections revealed a higher intensity around the thalamus than the cortex and hippocampus regions while the male brain sections showed D-AIP intensities in the reverse order, hippocampus>cortex>thalamus, respectively. In the control, i.e. in the absence of D-AIP, the heat map showed an almost uniformly blue-colored background as expected for brain sections from PBS-dosed control female and male mice.

Freshly monomerized Aβ42 was co-incubated with D-AIP for 24 h at three different D-AIP:Aβ42 ratios, i.e. equimolar, 4-fold and 10-fold molar excess of Aβ42 (FIG. 21). The tetramer was the minimal unit required to meet the steric and spatial constraints to bind to the groove of low-n oligomeric forms. The immediate presence of the ThT binding to low-n oligomers is indicated by the high signal of fluorescence intensity at time 0 (FIG. 21). The ThT fluorescence signal was monitored over 24 h in an in situ real-time ThT assay (FIG. 21A). Co-incubation with D-AIP significantly reduced the fluorescence to the same extent over approximately 10 h at all molar D-AIP:Aβ42 ratios tested compared to the control (FIG. 21A). This result implies that all D-AIP:Aβ42 ratios affected equally well the primary nucleation phase of the three phases described in theory for Aβ42 aggregation, i.e., primary nucleation, elongation and secondary nucleation.

Between 10 h and 24 h incubation time, a clear separation of fluorescent signal curves became obvious, showing that the ratio 1:4 was most efficient in reducing the ThT signal, followed by 1:10 and 1:1 (FIG. 22A). This data indicates that the aggregation is affected by D-AIP during elongation and secondary nucleation phases and is only slightly modulated by the ratio. Consequently, TEM analysis was used to confirm that D-AIP not only inhibits the conversion of low-n Aβ42 oligomers into higher forms of aggregates after 24 h, but also affected phases of fibril growth (FIG. 22). TEM revealed dense fibrils with long, thick, branch-like structures for freshly monomerized Aβ42 in the absence of D-AIP (FIG. 22A) whereas fibril maturation was inhibited by D-AIP as indicated by short strand-like structures (FIG. 22B) while denser fibrils with long, thick, branch-like structures were observed in the absence of D-AIP (FIG. 22A). MALDI-TOF MS spectra of Aβ42 peptides co-incubated with D-AIP support the conclusion that the inhibitory effect of D-AIP on early aggregation steps is due to a direct binding of D-AIP not only to tetramers but also to pentamers and hexamers of Aβ42 (FIGS. 22H and 22I). This finding explains why the different ratios of D-AIP tested, including the highest ratio of 1:10 of D-AIP:Aβ42, almost equally well attenuated Aβ42 aggregation where Aβ42 is always present as a mixture of low-n Aβ42 oligomers.

To further analyze D-AIP effects on fibril growth, D-AIP were co-incubated with Aβ42 pre-aggregated for 24 h and monitored the ThT fluorescence signal for another 24 h (FIG. 21B). The ThT fluorescence of Aβ42 incubated alone increased rapidly after the equilibration period and reached a plateau at 36 h incubation time indicating a saturable interaction between ThT and Aβ42 fibrils (FIG. 22B). The addition of D-AIP led to a decrease in the ThT fluorescence (FIG. 22B), suggesting an efficient D-AIP/Aβ42 ratio-independent inhibition of fibril maturation. After 36 h, there was a stoichiometric and saturable interaction between ThT and amyloid fibrils which is evident from the plateaus of the in situ ThT fluorescence curves. In line with this, TEM micrographs of Aβ42 alone taken after 48 h revealed dense matured fibrils (FIG. 22D), fibril formation indicated that mature fibrils exist with diameters of 10 nm after 24 h and 8 nm after 48 h (FIG. 22E). D-AIP significantly affected further mature fibrils formation of pre-aggregated Aβ42 between 24 h and 48 h (FIG. 22E) giving a combination of stunted fibrillar and prefibrillar assemblies with an enlarged fibril width of approx. 18 nm (FIG. 22C). In contrast, Aβ42 incubated for 48 h showed dense mature fibrils (FIG. 22D). The significantly greater width when compared to the other conditions, may be indicative of a novel interaction of D-AIP with Aβ42 fibrils allowing lateral associations which is distinct from co-incubation conditions with freshly monomerized Aβ42 when longitudinal interaction is impaired.

While the present disclosure has been described in connection with specific embodiments thereof, it will be understood that it is capable of further modifications and this application is intended to cover any variations, uses, or adaptations, including such departures from the present disclosure as come within known or customary practice within the art and as may be applied to the essential features hereinbefore set forth, and as follows in the scope of the appended claims.

---

What is claimed is:

1. A method of diagnosing and treating Alzheimer's disease in a patient with mild cognitive impairment (MCI), the method comprising the following steps:

(a) obtaining a sample from the patient wherein the sample is a cerebrospinal fluid (CSF) sample;

(b) detecting a concentration of amyloid-β34 (Aβ34) in the sample of step (a) by contacting the sample with an anti-Aβ34 antibody and detecting binding between Aβ34 and the anti-Aβ34 antibody with an immunoassay;

(c) detecting a concentration of amyloid-β42 (Aβ42) in the sample of step (a) by contacting the sample with an anti-Aβ42 antibody and detecting binding between Aβ42 and the anti-Aβ42 antibody with the immunoassay;

(d) determining a concentration ratio of Aβ34/Aβ42 based on the concentration of Aβ34 detected in step (b) and the concentration of Aβ42 detected in step (c), wherein when the concentration ratio of Aβ34/Aβ42 is more than 0.245, the patient is diagnosed as having Alzheimer's disease; and (e) administering to the patient diagnosed as having Alzheimer's disease a treatment selected from the group consisting of an inhibitor of β-site amyloid precursor protein (APP) cleaving enzyme 1 (BACE1) and a synthetic 8-amino acid Aβ42-oligomer interacting Peptide (AIP).

2. The method of claim 1, wherein the anti-Aβ34 antibody specifically binds to an epitope of Aβ34 protein consisting of SEQ ID NO: 5 and/or the C-terminal end of Aβ34.

3. The method of claim 1, wherein the anti-Aβ34 antibody is selected from the group consisting of a humanized antibody, a monoclonal antibody and a polyclonal antibody.

4. The method of claim 1, wherein the anti-Aβ34 antibody comprises a) heavy chain encoded by a DNA sequence consisting of SEQ ID NO: 1;

b) a heavy chain amino acid sequence consisting of SEQ ID NO: 2;

c) a light chain encoded by a DNA sequence consisting of SEQ ID NO: 3;

d) a light chain amino acid sequence consisting of SEQ ID NO: 4;

e) a sequence with at least 70% sequence identity to a), b) c) or d); or f) a combination thereof.

5. The method of claim 1, wherein the anti-Aβ34 antibody further comprises a fluorochrome or a label.

6. The method of claim 1, wherein the immunoassay is selected from the group consisting of a radioimmunoassay, a Western blot assay, an immunofluorescence assay, an enzyme immunoassay, an immunoprecipitation assay, a chemiluminescence assay, an electrochemiluminescence assay, an immuno histochemical assay, an immunoelectrophoresis assay, a dot blot assay, and a slot blot assay.

7. The method of claim 1, wherein the 8-amino acid Aβ42-oligomer interacting Peptide (AIP) is D-AIP consisting of D-amino acids of SEQ ID NO: 6.

8. The method of claim 7, wherein the D-AIP is administered by a route of administration selected from the group consisting of parenteral, intravenous, oral, subcutaneous, intra-arterial, intracranial, intrathecal, intraperitoneal, topical, intranasal and intramuscular.

\* \* \* \* \*